US009403001B2

(12) United States Patent
Simon et al.

(10) Patent No.: US 9,403,001 B2
(45) Date of Patent: Aug. 2, 2016

(54) NON-INVASIVE MAGNETIC OR ELECTRICAL NERVE STIMULATION TO TREAT GASTROPARESIS, FUNCTIONAL DYSPEPSIA, AND OTHER FUNCTIONAL GASTROINTESTINAL DISORDERS

(71) Applicant: Electrocore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: Electrocore, LLC, Basking Ridge, NJ (US)

( * ) Notice: Subject to any disclaimer, the term of this patent is extended or adjusted under 35 U.S.C. 154(b) by 0 days.

(21) Appl. No.: 13/731,035

(22) Filed: Dec. 30, 2012

(65) Prior Publication Data

US 2013/0131753 A1 May 23, 2013

Related U.S. Application Data

(63) Continuation-in-part of application No. 13/222,087, filed on Aug. 31, 2011, now Pat. No. 9,174,066, and a continuation-in-part of application No. 13/183,765, filed on Jul. 15, 2011, now Pat. No. 8,874,227,
(Continued)

(51) Int. Cl.
*A61N 1/36* (2006.01)
*A61N 1/40* (2006.01)
(Continued)

(52) U.S. Cl.
CPC .............. *A61N 1/36007* (2013.01); *A61N 1/36* (2013.01); *A61N 1/36014* (2013.01);
(Continued)

(58) Field of Classification Search
CPC .................... A61N 1/36007; A61N 1/0456
See application file for complete search history.

(56) References Cited

U.S. PATENT DOCUMENTS 3,590,810 A * 7/1971 Kopecky .................... 600/396
4,196,737 A 4/1980 Bevilacqua
(Continued)

FOREIGN PATENT DOCUMENTS

| WO | WO 93/01862 | 2/1993 |
|---|---|---|
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Michael Kahelin
(74) *Attorney, Agent, or Firm* — Dentons US LLP

(57) ABSTRACT

Devices, systems and methods are disclosed for treating or preventing gastroparesis, functional dyspepsia, and other functional gastrointestinal disorders. The methods comprise transmitting impulses of energy non-invasively to selected nerve fibers, particularly those in a vagus nerve. The methods provide damaged interstitial cells of Cajal (ICC) with trophic factors via vagal afferent nerve fibers, thereby reversing ICC damage, and as a consequence improving gastric motility. The methods also increase levels of inhibitory neurotransmitters in the brain so as to decrease neural activity within the area postrema, or they deactivate a resting state neural network containing parts of the anterior insula and anterior cingulate cortex, which will thereby reduce abnormal interoception and visceral hypersensitivity.

16 Claims, 11 Drawing Sheets

Related U.S. Application Data application No. 13/731,035, which is a continuation-in-part of application No. 13/075,746, filed on Mar. 30, 2011, now Pat. No. 8,874,205.

(60) Provisional application No. 61/488,208, filed on May 20, 2011, provisional application No. 61/451,259, filed on Mar. 10, 2011.

(51) Int. Cl.
- *A61N 2/00* (2006.01)
- *A61N 2/02* (2006.01)
- *A61N 1/20* (2006.01)
- *A61N 1/04* (2006.01)

(52) U.S. Cl.
CPC .............. *A61N 1/0456* (2013.01); *A61N 1/205* (2013.01); *A61N 1/40* (2013.01); *A61N 2/006* (2013.01); *A61N 2/02* (2013.01)

(56) References Cited

U.S. PATENT DOCUMENTS

| | | | |
|---|---|---|---|
| 5,458,141 A | 10/1995 | Neil | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0137644 A1* | 6/2005 | Boveja et al. ................... 607/40 |
| 2006/0074284 A1 | 4/2006 | Juola et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0051852 A1 | 2/2008 | Dietrich et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0157149 A1 | 6/2009 | Wahlgren et al. | |
| 2009/0234419 A1 | 9/2009 | Maschino et al. | |
| 2009/0287035 A1 | 11/2009 | Dietrich et al. | |
| 2010/0286553 A1* | 11/2010 | Feler et al. ................... 600/554 |
| 2011/0046432 A1 | 2/2011 | Simon et al. | |
| 2011/0152967 A1* | 6/2011 | Simon et al. ................... 607/45 |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2011/0276112 A1* | 11/2011 | Simon et al. ................... 607/72 |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

NON-INVASIVE MAGNETIC OR ELECTRICAL NERVE STIMULATION TO TREAT GASTROPARESIS, FUNCTIONAL DYSPEPSIA, AND OTHER FUNCTIONAL GASTROINTESTINAL DISORDERS

CROSS REFERENCE TO RELATED APPLICATIONS

The present application is a Continuation in Part of: (1) U.S. Nonprovisional application Ser. No. 13/222,087 filed Aug. 31, 2011; now U.S. Pat. No. 9,174,066 issued Nov. 3, 2015; (2) U.S. Nonprovisional application Ser. No. 13/183,765 filed Jul. 15, 2011, now U.S. Pat. No. 8,874,227 issue Oct. 28, 2014, which claims the benefit of U.S. Provisional Application No. 61/488,208 filed May 20, 2011; and (3) U.S. Nonprovisional application Ser. No. 13/075,746 filed Mar. 30, 2011, now U.S. Pat. No. 8,874,205 issued Oct. 28, 2014, which claims the benefit of U.S. Provisional Application 61/451,259 filed Mar. 10, 2011; each of which is incorporated herein by reference in its entirety.

BACKGROUND OF THE INVENTION

The field of the present invention relates to the delivery of energy impulses (and/or fields) to bodily tissues for therapeutic purposes. The invention relates more specifically to devices and methods for treating conditions associated with gastroparesis, functional dyspepsia, and functional gastrointestinal disorders generally. The energy impulses (and/or fields) that are used to treat those conditions comprise electrical and/or electromagnetic energy, delivered non-invasively to the patient.

The use of electrical stimulation for treatment of medical conditions is well known. For example, electrical stimulation of the brain with implanted electrodes has been approved for use in the treatment of various conditions, including pain and movement disorders such as essential tremor and Parkinson's disease.

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92 (2001):505-513; U.S. Pat. No. 6,871,099, entitled Fully implantable microstimulator for spinal cord stimulation as a therapy for chronic pain, to WHITEHURST, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009): 1042-1060; GROVES D A, Brown V J. Vagal nerve stimulation: a review of its applications and potential mechanisms that mediate its clinical effects. Neurosci Biobehav Rev 29 (2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N.Y. Acad. Sci. 993 (2003):1-13; LABINER, D. M., Ahern, G. L. Vagus nerve stimulation therapy in depression and epilepsy: therapeutic parameter settings. Acta. Neurol. Scand. 115 (2007):23-33].

Many such therapeutic applications of electrical stimulation involve the surgical implantation of electrodes within a patient. In contrast, devices used for the medical procedures that are disclosed herein do not involve surgery. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g, beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body. An electric field is induced at a distance causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that are disclosed herein are relatively simpler devices that use considerably smaller currents within the stimulator coils. Accordingly, they are intended to satisfy the need for simple-to-use and less expensive non-invasive magnetic stimulation devices, for use in treating gastroparesis or functional dyspepsia, as well as use in treating other conditions.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In the present invention, noninvasive electrical and/or magnetic stimulation of a vagus nerve is used to treat functional gastrointestinal disorders, which are defined as follows. Patients frequently consult a physician after experiencing gastrointestinal (GI) symptoms such as pain, nausea, vomiting, bloating, diarrhea, constipation, or difficult passage of food or feces. Tests are then performed in an effort to find an organic or structural explanation for the symptoms, such as an infection, tumor, structural blockage, metabolic abnormality or inflammation. When the tests do not reveal any such organic etiology or structural lesion, the patient is diagnosed as having a functional gastrointestinal disorder (FGID), which is to say, a GI disorder in which there is "no known structural (i.e, no pathological or radiological) abnormalities, or infectious, or metabolic causes". Examples of FGIDs are irritable bowel syndrome, functional dyspepsia and chronic constipation.

Until about thirty years ago, functional gastrointestinal disorders were considered undiagnosed, uninvestigated, idiopathic or cryptogenic, or they were simply correlated with lifestyle or psychological influences such as excessive psychosocial stress, because no organic causes for their symptoms could be identified. In this regard, FGIDs share the absence of a straightforward, well-defined pathophysiological cause with other non-GI disorders, such as chronic fatigue syndrome, fibromyalgia, and chronic regional pain disorder [LEVY R L, Olden K W, Naliboff B D, Bradley L A, Francisconi C, Drossman D A, Creed F. Psychosocial aspects of the functional gastrointestinal disorders. Gastroenterology 130(5, 2006):1447-1458; KIM S E, Chang L. Overlap between functional GI disorders and other functional syndromes: what are the underlying mechanisms? Neurogastroenterol Motil 24(10, 2012):895-913; Clive H WILDER-SMITH. The balancing act: endogenous modulation of pain in functional gastrointestinal disorders. Gut 60 (2011):1589-1599].

However, more recently, it is appreciated that a FGID is the clinical product of an interaction of psychosocial factors with an altered gut physiology that involves complex feedback between the gut and the central nervous system (the gut-brain axis). For example, some patients may experience a transient minor infection or inflammation in their GI tract that would not produce symptoms in a normal individual, but because the digestive and nervous systems of the FGID patient have become hypersensitive, the FGID patient does in fact develop GI symptoms [Douglas A. DROSSMAN. The functional gastrointestinal disorders and the Rome III process. Gastroenterology 130 (2006):1377-1390; WOOD J D, Alpers D H, Andrews P L. Fundamentals of neurogastroenterology. Gut 45 (Supp) 2, 1999):II6-II16; GRUNDY D, Al-Chaer E D, Aziz Q, Collins S M, Ke M, Taché Y, Wood J D. Fundamentals of neurogastroenterology: basic science. Gastroenterology 130(5, 2006):1391-1411; GEBHART G F. Pathobiology of visceral pain: molecular mechanisms and therapeutic implications IV. Visceral afferent contributions to the pathobiology of visceral pain. Am J Physiol Gastrointest Liver Physiol 278(6, 2000):G834-838; CRAIG A D. How do you feel? Interoception: the sense of the physiological condition of the body. Nat Rev Neurosci 3(8, 2002):655-666; BIELEFELDT K, Christianson J A, Davis B M. Basic and clinical aspects of visceral sensation: transmission in the CNS. Neurogastroenterol Motil 17(4, 2005):488-499; MAYER E A, Naliboff B D, Craig A D. Neuroimaging of the brain-gut axis: from basic understanding to treatment of functional GI disorders. Gastroenterology 131(6, 2006):1925-42; ANAND P, Aziz Q, Willert R, van Oudenhove L. Peripheral and central mechanisms of visceral sensitization in man. Neurogastroenterol Motil 19(1 Suppl, 2007):29-46; MAYER E A. The neurobiology of stress and gastrointestinal disease. Gut 47(6, 2000): 861-869; MAYER E A, Collins S M. Evolving pathophysiologic models of functional gastrointestinal disorders. Gastroenterology 122(7, 2002):2032-2048; MAYER E A, Tillisch K, Bradesi S. Review article: modulation of the brain-gut axis as a therapeutic approach in gastrointestinal disease. Aliment Pharmacol Ther 24(6, 2006):919-933; HOLZER P, Schicho R, Holzer-Petsche U, Lippe I T. The gut as a neurological organ. Wien Klin Wochenschr 113(17-18, 2001):647-60; MULAK A, Bonaz B. Irritable bowel syndrome: a model of the brain-gut interactions. Med Sci Monit 10(4, 2004): RA55-RA62; JONES M P, Dilley J B, Drossman D, Crowell M D. Brain-gut connections in functional GI disorders: anatomic and physiologic relationships. Neurogastroenterol Motil 18(2, 2006):91-103; MOSHIREE B, Zhou Q, Price D D, Verne G N. Central sensitisation in visceral pain disorders. Gut 55(7, 2006):905-908; ZHOU Q, Verne G N. New insights into visceral hypersensitivity—clinical implications in IBS. Nat Rev Gastroenterol Hepato 8(6, 2011):349-355].

The present invention is concerned primarily with a stomach-related type of FGID—functional dyspepsia, which has four specific symptoms that are thought to originate from the gastroduodenal region (viz., postprandial fullness, early satiation, epi-gastric pain, and epigastric burning). The invention is also concerned with a condition that is common among functional dyspepsia patients, in which there is delayed emptying of the stomach into the intestine. The medical term for such delayed stomach emptying in the absence of structural blockage is gastropareis (partial paralysis of the stomach), which is often accompanied by chronic or intermittent nausea, vomiting, early satiety, abdominal distention after eating, and/or abdominal pain typically following meals [MIWA H. Why dyspepsia can occur without organic disease: pathogenesis and management of functional dyspepsia. J Gastroenterol 47(8, 2012):862-871; TACK J, Lee K J. Pathophysiology and treatment of functional dyspepsia. J Clin Gastroenterol 39(5 Suppl 3, 2005):S211-6; TACK J, Masaoka T, Janssen P. Functional dyspepsia. Curr Opin Gastroenterol 27(6, 2011):549-557; TACK J, Talley N J, Camilleri M, Holtmann G, Hu P, Malagelada J R, Stanghellini V. Functional gastroduodenal disorders. Gastroenterology 130 (5, 2006):1466-1479; Rita BRUN and Braden Kuo. Functional dyspepsia. Therap Adv Gastroenterol 3(3, 2010): 145-

164; AGREUS L. Natural history of dyspepsia. Gut 50 (Suppl 4, 2002):iv2-9; GEERAERTS B, Tack J. Functional dyspepsia: past, present, and future. J Gastroenterol 43(4, 2008): 251-255; LOYD R A, McClellan D A. Update on the evaluation and management of functional dyspepsia. Am Fam Physician 83(5, 2011):547-552; HASLER W L. Gastroparesis: symptoms, evaluation, and treatment. Gastroenterol Clin North Am 36(3, 2007):619-647; Olga HILAS. Management of Gastroparesis. US Pharm 36(12, 2011):HS15-HS18; MASAOKA T, Tack J. Gastroparesis: current concepts and management. Gut Liver 3(3, 2009):166-73; PATRICK A, Epstein O. Review article: gastroparesis. Aliment Pharmacol Ther. 2008 May; 27(9, 2008):724-740; WASEEM S, Moshiree B, Draganov P V. Gastroparesis: current diagnostic challenges and management considerations. World J Gastroenterol 15(1, 2009):25-37; VITTAL H, Farrugia G, Gomez G, Pasricha P J. Mechanisms of disease: the pathological basis of gastroparesis—a review of experimental and clinical studies. Nat Clin Pract Gastroenterol Hepatol 4(6, 2007):336-346].

Despite the fact that at least some aspect each FDIG is different from the other FDIG disorders, they nevertheless may share other features, and they are frequently comorbid, so that they may be considered as a group. Furthermore, symptomatic and pathophysiological aspects that different FDIGs have in common may make it possible to treat them with similar therapeutic methods. Consequently, it is understood that the devices and methods of the present invention may be applicable to many types of FGID, as organized by the Rome III classification: A. Functional esophageal disorders (A1. Functional heartburn; A2. Functional chest pain of presumed esophageal origin; A3. Functional dysphagia; A4. Globus); B. Functional gastroduodenal disorders (B1. Functional dyspepsia; B1a. Postprandial distress syndrome; B1b. Epigastric pain syndrome; B2. Belching disorders; B2a. Aerophagia; B2b. Unspecified excessive belching; B3. Nausea and vomiting disorders; B3a. Chronic idiopathic nausea; B3b. Functional vomiting; B3c. Cyclic vomiting syndrome; B4. Rumination syndrome in adults or Merycism); C. Functional bowel disorders (C1. Irritable bowel syndrome; C2. Functional bloating; C3. Functional constipation; C4. Functional diarrhea; C5. Unspecified functional bowel disorder; D. Functional abdominal pain syndrome; E. Functional gallbladder and Sphincter of Oddi (SO) disorders (E1. Functional gallbladder disorder; E2. Functional biliary SO disorder; E3. Functional pancreatic SO disorder); F. Functional anorectal disorders (F1. Functional fecal incontinence; F2. Functional anorectal pain; F2a. Chronic proctalgia; F2a1. Levator ani syndrome; F2a2. Unspecified functional anorectal pain; F2b. Proctalgia fugax; F3. Functional defecation disorders; F3a. Dyssynergic defecation; F3b. Inadequate defecatory propulsion; G. Various GI functional disorders in neonates and toddlers; and H. Various functional GI disorders in children and adolescents.

FGIDs account for 41% of diagnoses in GI specialty practices, among which irritable bowel syndrome (IBS) is the most common. IBS comprises 12% of the diagnoses made by primary care physicians generally and 28% of the diagnoses in GI practices. Its prevalence is in the range 5-25%, and it accounts for 36% of all visits to gastroenterologists [CHANG L. Review article: epidemiology and quality of life in functional gastrointestinal disorders. Aliment Pharmacol Ther 20 (Suppl 7, 2004):31-39; DROSSMAN D A, Li Z, Andruzzi E, et al. U.S. householder survey of functional gastrointestinal disorders. Prevalence, sociodemography, and health impact. Dig Dis Sci. 38(9, 1993):1569-1580; MERTZ H R. Irritable bowel syndrome. N Engl J Med 349(22, 2003):2136-2146; CAMILLERI M. Treating irritable bowel syndrome: overview, perspective and future therapies. Br J Pharmacol 141(8, 2004):1237-1248; DROSSMAN D A. Review article: an integrated approach to the irritable bowel syndrome. Aliment Pharmacol Ther 13 (Suppl 2, 1999):3-14].

Dyspepsia also has a high prevalence. Patients often experience dyspeptic symptoms of short duration and mild severity, and are therefore self-managed, with less than half of dyspepsia sufferers seeking medical care for their complaints. Even so, there are over 2 million physician consultations for dyspepsia annually in the United States alone. Dyspepsia has a prevalence of approximately 25% in Western countries, even after the exclusion of individuals with typical gastroesophageal reflux disease (GERD) symptoms. The annual incidence of dyspepsia is approximately 9-10%, and 15% of patients have chronic (>3 months in a year), frequent (>3 episodes per week) often severe symptoms. Functional dyspepsia is the most common cause of dyspeptic symptoms (approximately 75%), with the remainder of dyspepsia cases having an organic cause such as a peptic ulcer, reflux disease, etc. [Andrew Seng Boon CHUA. Epidemiology of functional dyspepsia: A global perspective. World J Gastroenterol 12(17, 2006): 2661-2666; SHAIB Y, El-Serag H B. The prevalence and risk factors of functional dyspepsia in a multiethnic population in the United States. Am J Gastroenterol 99(11, 2004):2210-2216; OUSTAMANOLAKIS P, Tack J. Dyspepsia: organic versus functional. J Clin Gastroenterol 46(3, 2012):175-90; SANDER G B, Mazzoleni L E, Francesconi C F, et al. Influence of organic and functional dyspepsia on work productivity: the HEROES-DIP study. Value in Health 14(5 Suppl 1, 2011):S126-S129].

A difficulty in interpreting the epidemiological data mentioned above is that considerable symptomatic and pathophysiological overlap exists between FDIG disorders. Thus, despite their classification as different entities, IBS and functional dyspepsia may also be regarded as different manifestations of a larger pathophysiological entity that encompasses even non-FGID disorders with which the FDIG disorders may be comorbid, such as overactive bladder [FRISSORA C L, Koch K L. Symptom overlap and comorbidity of irritable bowel syndrome with other conditions. Curr Gastroenterol Rep 7(4, 2005):264-271; Laura NODDIN, Michael Callahan, and Brian E. Lacy. Irritable Bowel Syndrome and Functional Dyspepsia: Different Diseases or a Single Disorder With Different Manifestations? Med Gen Med 7(3, 2005): 17, pp. 1-10; WANG A, Liao X, Xiong L, Peng S, Xiao Y, Liu S, Hu P, Chen M. The clinical overlap between functional dyspepsia and irritable bowel syndrome based on Rome III criteria. BMC Gastroenterol 8 (2008): 43, pp. 1-7; BALBOA A, Mearin F, Badía X, et al. Impact of upper digestive symptoms in patients with irritable bowel syndrome. Eur J Gastroenterol Hepatol 18(12, 2006):1271-1277; DEVRIES D R, Van Herwaarden M A, Baron A, Smout A J, Samsom M. Concomitant functional dyspepsia and irritable bowel syndrome decrease health-related quality of life in gastroesophageal reflux disease. Scand J Gastroenterol 42(8, 2007):951-956; EVANS P R, Bak Y T, Shuter B, Hoschl R, Kellow J E. Gastroparesis and small bowel dysmotility in irritable bowel syndrome. Dig Dis Sci 42(10, 1997):2087-2093; QUIGLEY E M. Review article: gastric emptying in functional gastrointestinal disorders. Aliment Pharmacol Ther 20 (Suppl 7, 2004):56-60; ARO P, Talley N J, Ronkainen J, Storskrubb T, Vieth M, Johansson S E, Bolling-Sternevald E, Agréus L. Anxiety is associated with uninvestigated and functional dyspepsia (Rome III criteria) in a Swedish population-based study. Gastroenterology 137(1, 2009):94-100; HSU Y C, Liou J M, Liao S C, Yang T H, Wu H T, Hsu W L, Lin H J, Wang H P, Wu M S. Psychopathology and personality trait in subgroups of functional dyspepsia based on Rome III criteria. Am J Gastroenterol 104(10, 2009):2534-2542; SANTONICOLA A, Siniscalchi M, Capone P, Gallotta S, Ciacci C, Iovino P. Prevalence of functional dyspepsia and its subgroups in patients with eating disorders. World J. Gastroenterol. 18(32, 2012):4379-4385; MATSUZAKI J, Suzuki H, Fukushima Y, Hirata K, Fukuhara S, Okada S, Hibi T. High frequency of overlap between functional dyspepsia and overactive bladder. Neurogastroenterol Motil 24(9, 2012):821-827].

Similarly, the distinction between functional dyspepsia and gastroparesis is equivocal. Gastroparesis is a syndrome characterized by delayed gastric emptying in the absence of mechanical obstruction. The main symptoms include early satiety, nausea, vomiting, pain, and bloating. In one study, the frequency of symptoms was pain (89%), nausea (93%), early satiety (86%) and vomiting (68%). Gastroparesis is common, affecting up to 5 million individuals in the United States. The majority of patients are female (80%) and the mean age of onset is 34 years. Between 5 and 12 percent of patients with diabetes have symptoms that are attributable to gastroparesis [Baha MOSHIREE, Steven Bollipo, Michael Horowitz, and Nicholas J. Talley. Epidemiology of gastroparesis. Chapter 2 (pp. 11-22) In: Gastroparesis. Pathophysiology, Presentation and Treatment. H. P. Parkman and R. W. McCallum, eds. New York: Humana Press, 2012; JUNG H K, Choung R S, Locke G R 3rd, Schleck C D, Zinsmeister A R, Szarka L A, Mullan B, Talley N J. The incidence, prevalence, and outcomes of patients with gastroparesis in Olmsted County, Minnesota, from 1996 to 2006. Gastroenterology 136(4, 2009):1225-1233].

Gastroparesis is primarily (but not exclusively) a motility disorder of the stomach, in contrast to functional dyspepsia (FD), which is a functional disorder of the stomach with intertwined sensory and motility abnormalities. Nevertheless, although gastroparesis and FD are generally considered two distinct disorders, the distinction between them is blurred by the considerable overlap in symptoms and the recognition that delayed gastric emptying can be seen in FD. The symptoms of FD are directly caused by two major physiological abnormalities—abnormal gastric motility and visceral hypersensitivity—occurring in patients who have acquired excessive responsiveness to stress as a result of the environment during early life, genetic abnormalities, residual inflammation after gastrointestinal infections, or other causes, with the process modified by factors including psychophysiological abnormalities, abnormal secretion of gastric acid, *Helicobacter pylori* infection, diet, and lifestyle. Accordingly, the current (Rome III) diagnostic criteria subdivides FD into two categories—(i) meal-induced dyspeptic symptoms (postprandial distress syndrome [PDS], characterized by postprandial fullness and early satiation) and (ii) epigastric pain syndrome ([EPS], characterized by epi-gastric pain and burning). A rationale for the subdivision is that different treatment modalities may be most suitable for each subgroup: acid suppressive therapy in EPS, and therapy for PDS in which drugs are used to increase gastrointestinal movement (prokinetic therapy). Therefore, gastroparesis may be most closely associated with the PDS category of functional dyspepsia. In fact, some patients with mild abdominal pain, nausea, postprandial distress, and evidence of delayed emptying are considered to have functional dyspepsia by some clinicians and gastroparesis by others, based on a subjective assessment of how much visceral hypersensitivity versus dysmotility contributes to the symptoms. From a diagnostic standpoint, a presentation of predominant pain and less nausea is considered to be more typical of functional dyspepsia, whereas dominant nausea with minimal pain is more consistent with idiopathic gastroparesis [PARKMAN H P, Camilleri M, Farrugia G, et al. Gastroparesis and functional dyspepsia: excerpts from the AGA/ANMS meeting. Neurogastroenterol Motil 22(2, 2010):113-133; TALLEY N J, Locke G R 3rd, Lahr B D, Zinsmeister A R, Tougas G, Ligozio G, Rojavin M A, Tack J. Functional dyspepsia, delayed gastric emptying, and impaired quality of life. Gut 55(7, 2006):933-9; KINDT S, Dubois D, Van Oudenhove L, Caenepeel P, Arts J, Bisschops R, Tack J. Relationship between symptom pattern, assessed by the PAGI-SYM questionnaire, and gastric sensorimotor dysfunction in functional dyspepsia. Neurogastroenterol Motil 21(11, 2009):1183-1188 and e104-e105; John M. WO and Henry P. Parkman. Motility and Functional Disorders of the Stomach: Diagnosis and Management of Functional Dyspepsia and Gastroparesis. Practical Gastroenterology. December 2006: 23-48; STANGHELLINI V, De Giorgio R, Barbara G, Cogliandro R, Tosetti C, De Ponti F, Corinaldesi R. Delayed Gastric Emptying in Functional Dyspepsia. Curr Treat Options Gastroenterol 7(4, 2004):259-264].

In the remainder of this background section, current methods for treating functional dyspepsia and gastroparesis are described. As summarized here, they include pharmacological methods, the use of herbal medicines, biofeedback and breathing exercises, hypnosis, acupuncture, direct electrical stimulation of the stomach (gastric electrical stimulation or GES), direct electrical stimulation of the intestine, invasive vagus nerve stimulation, and deep brain stimulation. As evidenced by the large number of potential treatment methods that are in use, none of them works reliably, which motivates the new and potentially better methods that are disclosed here [TALLEY N J, Vakil N; Practice Parameters Committee of the American College of Gastroenterology. Guidelines for the management of dyspepsia. Am J Gastroenterol 100(10, 2005):2324-2337; North of England Dyspepsia Guideline Development Group. Dyspepsia. Managing dyspepsia in adults in primary care. Centre for Health Services Research. University of Newcastle upon Tyne. 21 Claremont Place. Newcastle upon Tyne. NE2 4AA. UK. 2004, pp. 1-288; SAAD R J, Chey W D. Review article: current and emerging therapies for functional dyspepsia. Aliment Pharmacol Ther 24(3, 2006):475-492; HASLER W L. Gastroparesis: symptoms, evaluation, and treatment. Gastroenterol Clin North Am 36(3, 2007):619-647; Olga HILAS. Management of Gastroparesis. US Pharm 36(12, 2011):HS15-HS18; MASAOKA T, Tack J. Gastroparesis: current concepts and management. Gut Liver 3(3, 2009):166-73; WASEEM S, Moshiree B, Draganov P V. Gastroparesis: current diagnostic challenges and management considerations. World J Gastroenterol 15(1, 2009):25-37].

Dietary approaches to treatment involve ingesting multiple small meals each day and consuming more liquid and less solid. Fatty food and carbonated beverages are avoided, and for patients who are diabetic, their diet is modified to treat the diabetes.

No drugs with established efficacy are definitive for treatment of functional dyspepsia and gastroparesis. However, gastrointestinal prokinetic drugs, which stimulate gastric smooth muscle contractions, have long been considered the drugs of choice. Traditional prokinetic agents are dopamine-2-receptor (D2) antagonists or 5-HT4 receptor agonists, e.g., cisapride (but now withdrawn from the market), domperidone, metoclopramide, and mosapride. Erythromycin is also used to enhance motility. H2 receptor antagonists, proton pump inhibitors, antiemetics and drugs to treat *H. Pylori* are also sometimes prescribed [TACK J, Lee K J. Pathophysiology and treatment of functional dyspepsia. J Clin Gastroenterol 39(5 Suppl 3, 2005):S211-6; MONKEMULLER K, Malfertheiner P. Drug treatment of functional dyspepsia. World J Gastroenterol 12(17, 2006):2694-2700; HASLER W L. Gastroparesis: symptoms, evaluation, and treatment. Gastroenterol Clin North Am 36(3, 2007):619-647].

Alternative medicine approaches are also used to treat functional dyspepsia and gastroparesis, including the use of herbal medicines, biofeedback, and hypnosis [Thompson COON J, Ernst E. Systematic review: herbal medicinal products for non-ulcer dyspepsia. Aliment Pharmacol Ther 16(10, 2002):1689-1699; HJELLAND I E, Svebak S, Berstad A, Flatabo G, Hausken T. Breathing exercises with vagal biofeedback may benefit patients with functional dyspepsia. Scand J Gastroenterol 42(9, 2007):1054-1062; CALVERT E L, Houghton L A, Cooper P, Morris J, Whorwell P J. Long-term improvement in functional dyspepsia using hypnotherapy. Gastroenterology 123(6, 2002):1778-85].

Acupuncture is also used to treat functional dyspepsia and gastroparesis. The sites of stimulation are usually RN12 (at the middle of the stomach), ST36 (on the front of the leg), PC6 (located on the wrist), and SP6 (on the medial aspect of the lower leg) [TAKAHASHI T. Acupuncture for functional gastrointestinal disorders. J Gastroenterol 41(5, 2006):408-417; ZHENG H, Tian X P, Li Y, Liang F R, et al. Acupuncture as a treatment for functional dyspepsia: design and methods of a randomized controlled trial. Trials 10 (2009):75, pp. 1-9; KIM K H, Kim T H, Choi J Y, Kim J I, Lee M S, Choi S M. Acupuncture for symptomatic relief of gastroparesis in a diabetic haemodialysis patient. Acupunct Med 28(2, 2010): 101-103; WANG C P, Kao C H, Chen W K, Lo W Y, Hsieh C L. A single-blinded, randomized pilot study evaluating effects of electroacupuncture in diabetic patients with symptoms suggestive of gastroparesis. J Altern Complement Med 14(7, 2008):833-839; IMAI K, Ariga H, Chen C, Mantyh C, Pappas T N, Takahashi T. Effects of electroacupuncture on gastric motility and heart rate variability in conscious rats. Auton Neurosci 138(1-2, 2008):91-98]. Despite the fact that a vagus nerve is not stimulated by the acupuncture as currently practiced, vagal activity is nevertheless said to be indirectly affected [OUYANG H, Yin J, Wang Z, Pasricha P J, Chen J D. Electroacupuncture accelerates gastric emptying in association with changes in vagal activity. Am J Physiol Gastrointest Liver Physiol 282(2, 2002):G390-G396].

Various devices have been used or proposed to treat functional gastrointestinal disorders and gastroparesis [GREENWAY F, Zheng J. Electrical stimulation as treatment for obesity and diabetes. J Diabetes Sci Technol 1(2, 2007):251-259]. The most well known among them is gastric electrical stimulation (GES), which stimulates stomach muscle directly, in a manner that is analogous to a cardiac pacemaker. Low-frequency/high-energy GES appears to work well in principle, but it is not presently suitable for routine clinical use. High-frequency/low-energy GES does not significantly modify gastric slow wave and motor activity and does not appear to consistently resolve the problem of delayed gastric emptying, but may it nevertheless resolve some symptoms. Therefore, GES is considered at best partially successful in treating gastroparesis [Mauro BORTOLOTTI. Gastric electrical stimulation for gastroparesis: A goal greatly pursued, but not yet attained. World J Gastroenterol 17(3, 2011): 273-282; McCALLUM R W, Dusing R W, Sarosiek I, Cocjin J, Forster J, Lin Z. Mechanisms of symptomatic improvement after gastric electrical stimulation in gastroparetic patients. Neurogastroenterol Motil 22(2, 2010):161-167, e50-e51; YIN J, Abell T D, McCallum R W, Chen J D. Gastric neuromodulation with Enterra system for nausea and vomiting in patients with gastroparesis. Neuromodulation 15(3, 2012): 224-231; SOFFER E, Abell T, Lin Z, Lorincz A, McCallum R, Parkman H, Policker S, Ordog T. Review article: gastric electrical stimulation for gastroparesis—physiological foundations, technical aspects and clinical implications. Aliment Pharmacol Ther 30(7, 2009):681-694; SONG G Q, Chen JD. Synchronized gastric electrical stimulation improves delayed gastric emptying in nonobese mice with diabetic gastroparesis. J Appl Physiol 103(5, 2007):1560-1564; LIU J, Qiao X, Chen J D. Vagal afferent is involved in short-pulse gastric electrical stimulation in rats. Dig Dis Sci 49(5, 2004):729-737; CHEN J H, Song G Q, Yin J, Sun Y, Chen J D. Gastric electrical stimulation reduces visceral sensitivity to gastric distention in healthy canines. Auton Neurosci 160(1-2, 2011):16-20; OGRADY G, Egbuji J U, Du P, Cheng L K, Pullan A J, Windsor J A. High-frequency gastric electrical stimulation for the treatment of gastroparesis: a meta-analysis. World J Surg 33(8, 2009):1693-1701]. GES is also disclosed in the patent literature, for example: U.S. Pat. No. 8,239,027, entitled Responsive gastric stimulator, to IMRAN; and U.S. Pat. No. 7,363,084, entitled Device for electrically stimulating stomach, to KUROKAWA et al.

In some patients, delayed emptying of the stomach may be due in part to delayed movement of chyme in the intestine, i.e., a downstream backing-up, such that intestinal movement that is promoted by electrical stimulation of the intestine itself may indirectly promote gastric emptying [XU J, Chen J D. Intestinal electrical stimulation improves delayed gastric emptying and vomiting induced by duodenal distension in dogs. Neurogastroenterol Motil 20(3, 2008):236-42]. As described below, a related mechanism is invoked by KNUDSEN et al in the form of "enteric rhythm management", wherein invasive vagus nerve stimulation is used to promote the effects of pancreatic exocrine secretion and bile on the composition and the digestion of intraduodenal chyme, thereby indirectly promoting gastric emptying through downstream effects. The present invention uses noninvasive rather than invasive vagus nerve stimulation, and physiological differences as compared with the KNUDSEN disclosure also arise because the present invention stimulates the vagus nerve at a different location and involves different mechanisms, but it is understood that the present invention might also produce such coordinated effects throughout the gastrointestinal system, thereby also underscoring the overlap between different forms of functional gastrointestinal disorders.

Deep brain electrical stimulation has also been used in connection with gastrointestinal problems, but only in conjunction with the treatment of another problem such as parkinsonism [ARAI E, Arai M, Uchiyama T, et al. Subthalamic deep brain stimulation can improve gastric emptying in Parkinson's disease. Brain 135 (Pt 5, 2012):1478-1485].

Magnetic stimulation of patients with gastrointestinal disorders has apparently not been performed for dyspepsia or gastroparesis, although it has been performed for lower digestive problems (on the buttocks) and for visceral pain (at the cerebral cortex) [LEE K J, Kim J H, Cho S W. Short-term effects of magnetic sacral dermatome stimulation for idiopathic slow transit constipation: sham-controlled, cross-over pilot study. J Gastroenterol Hepatol 21(1 Pt 1, 2006):47-53; LEFAUCHEUR J P. Use of repetitive transcranial magnetic stimulation in pain relief. Expert Rev Neurother 8(5, 2008): 799-808].

The literature on vagus nerve stimulation (VNS) generally teaches that its use may produce adverse gastrointestinal side effects, which is to say, most of the VNS literature teaches away from the present invention. Thus, nausea (14-20%), vomiting (13-18%) and dyspepsia (12-18%) are commonly reported adverse effects from implanted vagus nerve stimulators that are used to treat epilepsy and/or depression, although the side-effects are generally mild and usually do not warrant termination of the therapy. The prevalence of the side effects depends upon the parameters of the nerve stimulation (frequency, pulse-width, etc.). There is also one case report in which chronic diarrhea was associated with VNS, such that the diarrhea ceased after VNS therapy was terminated [HATTON K W, McLarney J T, Pittman T, Fahy B G. Vagal nerve stimulation: overview and implications for anesthesiologists. Anesth Analg 103(5, 2006):1241-1249; SANOSSIAN N, Haut S. Chronic diarrhea associated with vagal nerve stimulation. Neurology 58 (2002):330].

Nevertheless, SINCLAIR reported one clinical case demonstrating that invasive VNS might offer an alternative solution to dyspepsia resulting from impaired gastric emptying, or at least a treatment for symptoms of reflux [Rohna SINCLAIR and Rahul R. Bajekal. Vagal Nerve Stimulation and Reflux. Anesthesia & Analgesia 105(3, 2007): 884-885]. Invasive VNS to treat gastrointestinal conditions is also described in several patents. In U.S. Pat. No. 5,540,730, entitled Treatment of motility disorders by nerve stimulation, to TERRY, Jr. et al., stimulation of a vagus nerve in the vicinity of the patient's stomach is performed in response to the impedance of a selected part of the gastrointestinal system (as an indication of gastrointestinal status), in order to treat hypomobility or hypermobility. In U.S. Pat. No. 7,167,751, entitled Method of using a fully implantable miniature neurostimulator for vagus nerve stimulation to WHITEHURST et al. it is disclosed that: "As another example, the vagus nerve may be stimulated to relieve gastrointestinal disorders (such as including gastroesophageal reflux disease (GERD), fecal dysfunction, gastrointestinal ulcer, gastroparesis, and other gastrointestinal motility disorders." In U.S. Pat. No. 7,856, 273, entitled Autonomic nerve stimulation to treat a gastrointestinal disorder, to MASCHINO et al., a vagus nerve is electrically stimulated in order to treat a gastrointestinal disorder that may include a motility disorder. Invasive vagus nerve stimulation has also been combined with gastric electrical stimulation (GES) [U.S. Pat. No. 6,826,428, entitled Gastrointestinal electrical stimulation, to CHEN et al.].

In a series of patents and patent applications, KNUDSON and colleagues also describe invasive methods in which a vagus nerve is electrically stimulated in order to treat a variety of functional gastrointestinal disorders [All to KNUDSON et al.—U.S. Pat. No. 8,046,085, entitled Controlled vagal blockage therapy; U.S. Pat. No. 8,010,204, entitled Nerve blocking for treatment of gastrointestinal disorders; U.S. Pat. No. 7,986,995, entitled Bulimia treatment; U.S. Pat. No. 7,729, 771, entitled Nerve stimulation and blocking for treatment of gastrointestinal disorders; U.S. Pat. No. 7,720,540, entitled Pancreatitis treatment; U.S. Pat. No. 7,693,577, entitled Irritable bowel syndrome treatment; U.S. Pat. No. 7,630,769, entitled GI inflammatory disease treatment; U.S. Pat. No. 7,489,969, entitled Vagal down-regulation obesity treatment; U.S. Pat. No. 7,444,183, entitled Intraluminal electrode apparatus and method; U.S. Pat. No. 7,167,750, entitled Obesity treatment with electrically induced vagal down regulation; U.S. Pat. No. 7,844,338, entitled High frequency obesity treatment; U.S. Pat. No. 7,613,515, entitled High frequency vagal blockage therapy; US 20040176812, entitled Enteric rhythm management; US 20040172085, entitled Nerve stimulation and conduction block therapy]. These patents and applications differ from the present invention in several significant ways, including: they involve invasive methods, whereas the present invention involves noninvasive methods; in those patents, the site of vagus nerve stimulation is below a vagal innervation of the heart, e.g. a few centimeters below the diaphragm and proximal to stomach and pancreo/biliary innervation or around an internal body organ, whereas the present invention stimulates a vagus nerve at the neck, such that different vagal nerve fibers are stimulated in the present invention; stimulation in the present invention may generate proximate effects within the central nervous system (e.g., increasing afferent activity in A and B fibers of the vagus nerve to increase the levels of inhibitory neurotransmitters in the brainstem), whereas they produce their proximate effects within a gastrointestinal end organ through efferent nerves; they generally involve the use of one or more blocking electrodes (functionally speaking, a reversible vagotomy, wherein the block at least partially prevents nerve transmission across the site of the block), whereas the present invention does not; the present invention makes use of a bursting sinusoidal stimulation signal, whereas they do not; with regard to effects on gastric emptying, the present invention modulates the activity of interstitial cells of Cajal, whereas they do not; the present invention may modify resting state neural networks in the brain that are related to interoception, whereas they do not disclose any such mechanism. Many of these same distinctions apply to the other previously mentioned invasive VNS patents as well.

There also exists literature concerning noninvasive electrical stimulation methods as they relate to gastrointestinal disorders. Noninvasive methods have been described to treat symptoms that may accompany functional gastrointestinal disorders, e.g., nausea and vomiting. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal that may include nauses (sic) and vomiting. In patent publication US20080208266, entitled System and method for treating nausea and vomiting by vagus nerve stimulation, to LESSER et al., electrodes are used to stimulate the vagus nerve in the neck to reduce nausea and vomiting, or can be arranged near the chest or abdomen, so as to stimulate the esophagus, stomach, duodenum or intestines. However, because these methods are intended to treat morning sickness, side-effects of chemotherapy, etc., they are not designed specifically for treating for the forms of nausea and vomiting that are due to dyspepsia, gastroparesis, or other functional gastrointestinal disorders and do not simultaneously treat other symptoms of those disorders such as bloating. Consequently, those methods are intended to treat nausea and vomiting, but not a gastrointestinal disorder per se. For example, patients with gastroparesis, cyclic vomiting syndrome, and rumination syndrome may all experience different forms of vomiting, but the ECKERSON and the LESSER disclosures do not suggest which, if any, of these disorders may be treated by their methods. Furthermore, they teach devices and stimulation parameters that differ from what is disclosed here.

In contrast, WEINKAUF and colleagues used transcutaneous electrical stimulation to treat true gastroparesis. However, unlike the present invention, the electrical stimulation was performed on the back of the patients and did not involve the vagus nerve [WEINKAUF J G, Yiannopoulos A, Faul J L. Transcutaneous electrical nerve stimulation for severe gastroparesis after lung transplantation. J Heart Lung Transplant. 24(9, 2005):1444.e1-e3]. Similarly, KOKLU and colleagues used transcutaneous interferential current electrical stimulation to treat dyspeptic patients. However, also unlike the present invention, the electrical stimulation was performed on the back of the patients and did not involve stimulating a selected vagus nerve [KOKLUS, Köklü G, Ozgüçlü E, Kayani G U, Akbal E, Hasçelik Z. Clinical trial: interferential electric stimulation in functional dyspepsia patients—a prospective randomized study. Aliment Pharmacol Ther 31(9, 2010):961-968]. Patent publication US20100249859, entitled Methods for autonomic neuromodulation for the treatment of systemic disease, to DiLorenzo, discloses that "Modulation [of cranial nerves] is performed to modulate . . . gastroparesis, and other disorders."He includes noninvasive techniques among those used for neural modulation, but described them only as being the use of tactile stimulation, including light touch, pressure, vibration, and other modalities that may be used to activate the peripheral or cranial nerves. BALAJINS also describes noninvasive stimulation of the vagus nerve in the context of gastroenterology, but the stimulation involves sham feeding rather than electrical stimulation [BALAJI N S, Crookes P F, Banki F, Hagen J A, Ardill J E, DeMeester T R. A safe and noninvasive test for vagal integrity revisited. Arch Surg 137(8, 2002): 954-958; LUNDING J A, Nordström L M, Haukelid A O, Gilja O H, Berstad A, Hausken T. Vagal activation by sham feeding improves gastric motility in functional dyspepsia. Neurogastroenterol Motil 20(6, 2008):618-624]. In view of the foregoing, noninvasive electrical stimulation of a vagus nerve at the neck has not been performed to treat gastroparesis, functional dyspepsia, or other functional gastrointestinal conditions, despite the aforementioned potential advantages of noninvasive methods as compared with invasive methods.

In a commonly assigned, co-pending patent application, US20110125203, entitled Magnetic Stimulation Devices and Methods of Therapy, to SIMON et al., Applicants teach the use of a magnetic stimulation device, such as the ones disclosed here, to stimulate a vagus nerve in the neck to treat postoperative ileus, which is a form of hypomotility of the gastrointestinal tract in the absence of mechanical bowel obstruction. In that application, Applicants also teach use of a magnetic stimulation device to treat sphincter of Oddi dysfunction by stimulating a nerve plexus of fibers emanating from the tenth cranial nerve (the vagus nerve). In another commonly assigned, co-pending patent application, US20120101326, entitled Non-invasive electrical and magnetic nerve stimulators used to treat overactive bladder and urinary incontinence, to SIMON et al., applicants disclose the use of electrical nerve stimulation to affect pacemaker cells in the bladder that resemble the pacemaker cells in the stomach (interstitial cells of Cajal). The present disclosure extends those teachings to include additional methods and devices for the treatment or prevention of functional gastrointestinal disorders and gastroparesis.

SUMMARY OF THE INVENTION

The present invention involves devices and methods for the treatment of gastroparesis, functional dyspepsia, or other functional gastrointestinal disorders. In certain aspects of the invention, a device or system comprises an energy source of magnetic and/or electrical energy that is transmitted noninvasively to, or in close proximity to, a selected nerve of the patient to temporarily stimulate and/or modulate the signals in the selected nerve. In preferred embodiments of the invention, the selected nerve is a vagus nerve in the patient's neck.

Injury or loss of interstitial cells of Cajal (ICC) is the single most common pathophysiological feature found in patients with gastroparesis and other motility disorders of the gastrointestinal system. The ICC injury or loss may be due to a deficiency of trophic factors necessary for normal ICC maturation and survival. The present invention provides requisite trophic factors to gastric ICC cells and their progenitors, through electrical stimulation of a vagus nerve. In particular, it provides trophic factors to the ICC that are associated with intramuscular arrays, which are mechanoreceptors that are connected to vagus afferent nerve fibers. A method of the invention involves electrical stimulation of vagus afferent nerve fibers so as to imitate afferent signals that would have been transmitted by the vagal afferents in a normal individual. According to the invention, the afferent vagus nerve fiber will respond by providing to the damaged ICC what would have been the normal trophic factors, thereby reversing ICC degradation or loss, and as a consequence improving gastric motility.

Gastroparesis and functional dyspepsia are accompanied by abnormal interoception and visceral hypersensitivity. A method is disclosed that targets a front end of the interoceptive neural pathways, comprising the nucleus tractus solitarius, area postrema, and dorsal motor nucleus. The area postrema is well known as the medullary structure in the brain that controls vomiting, but it plays a more general role in mediating introceptive sensations, comprising also such sensations as postprandial fullness, bloating, pain, and nausea. Electrical stimulation of A and B fibers alone of the vagus nerve (using special stimulation waveforms and devices) produces increased levels of inhibitory neurotransmitters in the brainstem, which decreases signals that are conveyed to the parabrachial nucleus, VMb and VMpo of the interoceptive neural pathways. This inhibition is accomplished by causing the periaqueductal gray, raphe nucei, and locus ceruleus to release inhibitory neurotransmitters GABA, and/or serotonin, and/or norepinephrine, respectively, into the nucleus tractus solitarius, thereby opposing glutamate-mediated activation of the area postrema and dorsal motor nucleus by the nucleus tractus solitarius. Inhibition of the dorsal motor nucleus by these neurotransmitters also causes decreased neuronal activity in the area postrema, thereby leading to a reduction in abnormal interoception and visceral hypersensitivity.

The brain contains several neural networks that can be identified by brain imaging, which are known as resting state networks. Examples of such networks include the default mode network (DMN), the ventral attention network (VAN), and networks that include the anterior insula (AI) and anterior cingulate cortex (ACC). The AI/ACC networks are closely associated with interoception, which may be abnormal in patients with gastroparesis, functional dyspepsia, and other functional gastrointestinal disorders. The locus ceruleus is thought to project to all of the resting state networks. Vagus stimulation methods of the present invention increase norepinephrine levels in a resting state network, wherein a particular resting state network may be preferentially stimulated via the locus ceruleus, by using a vagus nerve stimulation waveform that entrains to the signature EEG pattern of that network. Depending on the distribution of adrenergic receptor subtypes within the resting state network, the vagus nerve stimulation may deactivate or activate the network. Deactivation of a resting state network may also be accomplished by activating another resting state network, which causes deactivation of other networks. According to the invention, AI/ACC-containing resting state networks may be deactivated either directly via the locus ceruleus or indirectly via activation of another resting network. In either case, deactivation of the AI/ACC-containing resting state network will diminish interoceptive symptoms of gastroparesis and/or functional dyspepsia. It is understood that all the above-mentioned mechanisms may apply to the treatment of other functional disorders as well.

For some patients, the stimulation may be performed for 30 minutes, and the treatment is performed several times a week for 12 weeks or longer, because the disease is a chronic situation that requires a substantial period to reverse the pathophysiology. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be selected as the course of the patient's disease changes. In preferred embodiments, the disclosed methods and devices do not produce clinically significant side effects, such as agitation or anxiety, or changes in heart rate or blood pressure.

In one embodiment, the method of treatment includes positioning the coil of a magnetic stimulator non-invasively on or above a patient's neck and applying a magnetically-induced electrical impulse non-invasively to the target region within the neck to stimulate or otherwise modulate selected nerve fibers. In another embodiment, surface electrodes are used to apply electrical impulses non-invasively to the target region within the neck to likewise stimulate or otherwise modulate selected nerve fibers. Preferably, the target region is adjacent to, or in close proximity with, the carotid sheath that contains a vagus nerve.

The non-invasive magnetic stimulator device is used to modulate electrical activity of a vagus nerve, without actually introducing a magnetic field into the patient. The preferred stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described below, shaping an elongated electrical field of effect.

In another embodiment of the invention, the stimulator comprises a source of electrical power and two or more remote electrodes that are configured to stimulate a deep nerve. The stimulator may comprise two electrodes that lie side-by-side within a hand-held enclosure, wherein the electrodes are separated by electrically insulating material. Each electrode is in continuous contact with an electrically conducting medium that extends from the interface element of the stimulator to the electrode. The interface element also contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

Treating or averting symptoms of gastroparesis and/or functional dyspepsia may be implemented within the context of control theory. A controller comprising, for example, one of the disclosed vagus nerve stimulators, a PID, and a feed-forward model, provides input to the patient via stimulation of one or both of the patient's vagus nerves. Feedforward models may be black box models, particularly models that make use of support vector machines. Data for training and exercising the models are from noninvasive physiological and/or environmental signals obtained from sensors located on or about the patient. The model predicts the onset of symptoms, which may be avoided prophylactically through use of vagus nerve stimulation. If the symptoms are in progress, the vagus nerve stimulation may terminate them.

The novel systems, devices and methods for treating gastroparesis and functional dyspepsia are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

DETAILED DESCRIPTION OF THE PREFERRED EMBODIMENTS

In one embodiment, a time-varying magnetic field, originating and confined to the outside of a patient, generates an electromagnetic field and/or induces eddy currents within tissue of the patient. In another embodiment, electrodes applied to the skin of the patient generate currents within the tissue of the patient. An objective of the invention is to produce and apply electrical impulses that interact with the signals of one or more nerves to achieve the therapeutic result of altering the course of gastroparesis, functional dyspepsia, and/or other functional gastrointestinal disorders. Much of the disclosure will be directed specifically to treatment of a patient by electromagnetic stimulation in or around a vagus nerve, with devices positioned non-invasively on or near a patient's neck. In particular, the present invention can be used to stimulate or otherwise modulate the activity of nerves that connect to certain structures and cells in the stomach, including intramuscular array (IMA) mechanoreceptors, interstitial cells of Cajal (ICC), and neurons of the enteric nervous system (ENS), as well as to modulate the activity of peripheral and central nerves that participate in interoception. However, it will be appreciated that the devices and methods of the present invention can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues.

Topics that are presented below in connection with the disclosure of the invention include the following: (1) Overview of physiological mechanisms by which vagus nerve stimulation may modulate the activity of nerves that connect to certain structures and cells in the stomach, including intramuscular array (IMA) mechanoreceptors, interstitial cells of Cajal (ICC), and neurons of the enteric nervous system (ENS), as well as modulate the activity of peripheral and central nerves that participate in interoception, thereby altering the course of gastroparesis, functional dyspepsia, and/or other functional gastrointestinal disorders; (2) Description of Applicant's magnetic and electrode-based nerve stimulating devices, describing in particular the electrical waveform used to stimulate a vagus nerve; (3) Preferred embodiments of the magnetic stimulator; (4) Preferred embodiments of the electrode-based stimulator; (5) Application of the stimulators to the neck of the patient; (6) Use of the devices with feedback and feedforward to improve treatment of individual patients.

Figure 1:
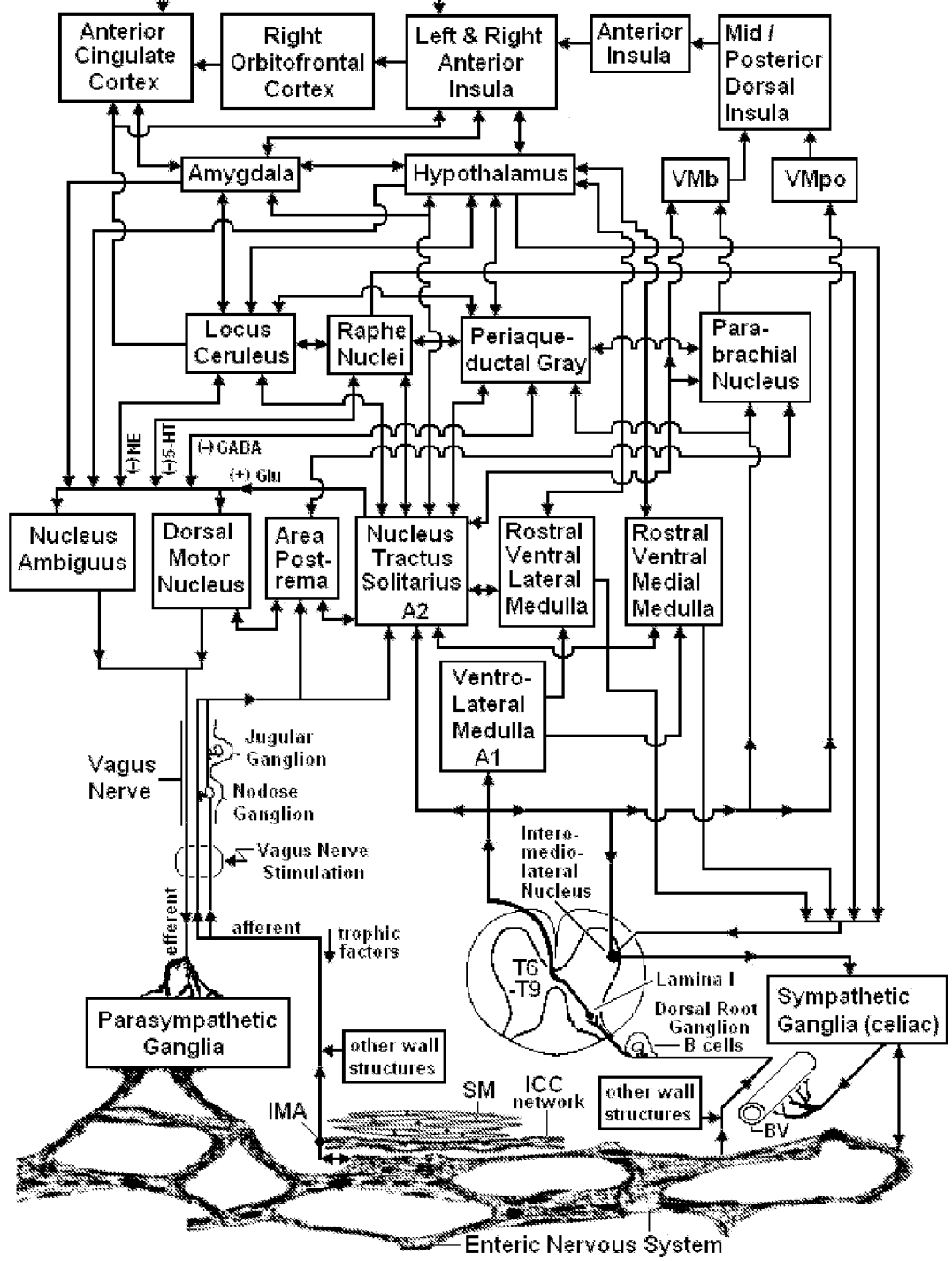
FIG. 1 shows structures within a patient's stomach and nervous system that may be abnormal in gastroparesis and/or functional dyspepsia, the physiology of which may be modulated by electrical stimulation of a vagus nerve.

Overview of Physiological Mechanisms Through which the Disclosed Vagus Nerve Stimulation Methods May be Used to Treat Patients with Gastroparesis and Functional Dyspepsia The present invention discloses methods and devices for electrically stimulating a vagus nerve noninvasively, in order to treat a patient for gastroparesis, functional dyspepsia, and/or other functional gastrointestinal conditions. FIG. 1 shows the location of the stimulation as "Vagus Nerve Stimulation," relative to connections with other anatomical structures that are affected by the stimulation [HOLZER P, Schicho R, Holzer-Petsche U, Lippe I T. The gut as a neurological organ. Wien Klin Wochenschr 113(17-18, 2001):647-660]. Physiological mechanisms that are involved, according to the invention, are described in the paragraphs that follow.

The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera, including the stomach.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system. Propagation of electrical signals in efferent and afferent directions are indicated by arrows in FIG. 1. If communication between structures is bidirectional, this is shown in FIG. 1 as a single connection with two arrows, rather than showing the efferent and afferent nerve fibers separately.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths.

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra. Most of the afferent connections from the gastrointestinal system involve the nodose ganglion.

Trophic substances may move within an axon in a direction opposite to the direction of electrical impulse propagation (anterograde axonal transport for afferent nerves, i.e, from nerve nucleus towards the periphery; retrograde axonal transport for efferent nerves, i.e, from periphery to nerve nucleus). For example, trophic substances may move towards the structure labeled as IMA in FIG. 1, along the mechanoreceptor afferent nerve having a cell body located in the nodose ganglion. According to the present invention, whether that nerve is electrically stimulated normally through the sensation of movement within the stomach, or by external electrical stimulation as in the present invention, that stimulation may cause trophic factors to reach the IMA to maintain, protect, or promote the structural integrity of the IMA and nearby objects, such as cells in what is labeled in FIG. 1 as "ICC network."

Vagal afferents traverse the brainstem in the solitary tract, with some eighty percent of the terminating synapses being located in the nucleus of the tractus solitarius (or nucleus tractus solitarii, nucleus tractus solitarius, or NTS, see FIG. 1). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5, 1991):A3-A52]. Such central projections are discussed below in connection with the gut-brain axis and interoception.

With regard to vagal efferent nerve fibers, two vagal components have evolved in the brainstem to regulate peripheral parasympathetic functions. The dorsal vagal complex, consisting of the dorsal motor nucleus and its connections (see FIG. 1), controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

In order to describe mechanisms by which the disclosed non-invasive vagus nerve stimulation may be used to treat gastroparesis and/or functional dyspepsia, we first summarize the relevant anatomy and innervation of the stomach, including innervation by the parasympathetic and sympathetic nervous systems [Arthur C. GUYTON and John E. Hall. General Principles of Gastrointestinal Function—Motility, Nervous Control, and Blood Circulation. pp. 771-778. In: Textbook of medical physiology, 11th ed. Philadelphia: Elsevier Saunders, 2006; Bruce M KOEPPEN and Bruce A Stanton. The gastric phase of the integrated response to a meal. Chapter 28 (pp. 504-515) in Berne & Levy physiology, 6th Edition. St. Louis, Mo.: Elsevier Mosby, 2010].

The stomach is a J-shaped tube with two openings (cardiac and pyloric orifices, opening to the esophagus and duodenum, respectively), two curvatures (greater and lesser), and two surfaces (anterior and posterior). The top of the stomach, the fundus, is dome shaped and is usually full of gas. The body (corpus) of the stomach lies below the fundus, and it connects to the lower pyloric region of the stomach (pyloric antrum and canal). Parasympathetic innervation of the stomach is supplied by branches of the vagus nerve. The anterior vagal trunk is a branch of the vagus nerve that contributes to the esophageal plexus. It consists primarily of fibers from the left vagus, but also contains a few fibers from the right vagus. The anterior gastric branches of anterior vagal trunk supply the stomach. One of its long branches runs from the lesser curvature of the stomach as far as the pyloric antrum to fan out into branches like the digits of a crow's foot to supply the pyloric antrum and the anterior wall of pyloric canal. The posterior vagal trunk is a branch of the vagus nerve that also contributes to the esophageal plexus. It consists primarily of fibers from the right vagus, but also contains a few fibers from the left vagus. The posterior gastric branches of the posterior vagal trunk supplies innervation to the posterior surface of stomach. Thus, electrical stimulation of the left versus right vagus nerve will preferentially stimulate particular regions of the stomach.

Various structures of the stomach are innervated by these vagal branches. Proceeding from the lumen of the stomach outward, the wall of the stomach comprises an inner mucosa (epithelium, lamina propria, and muscularis mucosae), a layer of fibrous connective tissue (submucosa, with innervation forming Meissner's plexus, also known as the submucosal plexus, and with a circulatory arteriolar and venous plexus), layers of smooth muscle (oblique, circular, and circular layers, with innervation between the latter layers forming Auerbach's plexus, also known as the myenteric plexus), and a serosal layer of connective tissue that is continuous with the surrounding peritoneum. The mucosa is densely packed with gastric glands, which contain cells that produce mucus, gastric acid, intrinsic factor, pepsinogen, gastrin, cholecystokinin, somatostatin, etc., that protect the stomach, aid in digestion, and signal digestive status within the stomach and to the rest of the body.

Gastric contractions and secretions are controlled in large measure by a semi-autonomous local nervous system (the enteric nervous system or ENS, also known as the intrinsic nervous system, see FIG. 1), comprising the above-mentioned submucosal plexus (Meissner's plexus) and myenteric plexus (Auerbach's plexus). The myenteric plexus controls mainly stomach wall movements, and the submucosal plexus controls mainly secretion and local blood flow. There are also minor plexuses beneath the serosa, within the circular smooth muscle and in the mucosa. These enteric plexuses connect to one another, as well as to extrinsic sympathetic and parasympathetic nerve fibers that can enhance or inhibit gastric muscle contractions and secretions. The enteric nervous system extends the entire length of the gastrointestinal system, thereby providing for physiological coordination between organs.

The enteric nervous system contains all the neuron types needed to perform independent reflex activity, even when it is dissociated from external sensory input or interaction with the sympathetic and parasympathetic nervous systems. Enteric sensory neurons receive information from sensory receptors in the mucosa and muscle. At least five different sensory receptors have been identified in the mucosa, which respond to mechanical, thermal, osmotic and chemical stimuli. Motor neurons within the enteric plexuses control gastrointestinal motility and secretion. Enteric interneurons integrate information from sensory neurons and use that information to control enteric motor neurons. The functional and chemical diversity of enteric neurons closely resembles that of the central nervous system. Furthermore, glial cells are an integral component of the enteric nervous system, and they outnumber enteric neurons. Consequently, the enteric nervous system may be regarded as a displaced part of the central nervous system that retains communication with the brain through sympathetic and parasympathetic afferent and efferent neurons [GOYAL R K, Hirano I. The enteric nervous system. N Engl J Med 334 (17, 1996):1106-1115; SURPRENANT A. Control of the gastrointestinal tract by enteric neurons. Annu Rev Physiol. 56 (1994):117-140; Marcello COSTA, John B Furness. Structure and Neurochemical Organization of the Enteric Nervous System. Compr Physiol 2011, Supplement 17: Handbook of Physiology, The Gastrointestinal System, Neural and Endocrine Biology (first published 1989): 97-109; SCHEMANN M. Control of gastrointestinal motility by the "gut brain"—the enteric nervous system. J Pediatr Gastroenterol Nutr 41(Suppl 1, 2005):54-6; BAGYANSZKI M, Bódi N. Diabetes-related alterations in the enteric nervous system and its microenvironment. World J Diabetes 3(5, 2012):80-93; GULBRANSEN B D, Sharkey K A. Novel functional roles for enteric glia in the gastrointestinal tract. Nat Rev Gastroenterol Hepatol 9(11, 2012):625-632].

Sensory nerve endings that originate in the gastric epithelium or stomach wall send afferent fibers to plexuses of the enteric system as described above, as well as to the vagus nerves. They also send fibers to the pre-vertebral ganglia of the sympathetic nervous system and to the spinal cord (See FIG. 1). Vagal afferents consist of two major types: mechanoreceptors which act largely as in-series tension receptors, and mucosal receptors which respond to mechanical stimulation of the mucosa and to a range of chemicals, mediators and nutrients. Vagal afferent axons ramify extensively, filling the enteric plexuses with plates of endings (intraganglionic laminar endings) and infiltrating muscle sheets (intramuscular arrays coursing with interstitial cells of Cajal). Parasympathetic afferent signals are central to vago-vagal reflexes that control gastric motility and secretion, and sympathetic afferent signals are important in regards to the sensation of gastric pain, as described below [BERTHOUD H R, Neuhuber W L. Functional and chemical anatomy of the afferent vagal system. Auton Neurosci 85(1-3, 2000):1-17; BLACKSHAW L A, Brookes S J, Grundy D, Schemann M. Sensory transmission in the gastrointestinal tract. Neurogastroenterol Motil 19(1 Suppl, 2007):1-19; ANDREWS P L, Sanger G J. Abdominal vagal afferent neurones: an important target for the treatment of gastrointestinal dysfunction. Curr Opin Pharmacol 2(6, 2002):650-656].

Preganglionic parasympathetic efferent nerve fibers to the stomach are carried almost entirely in the vagus nerves that arise from the dorsal motor nucleus (See FIG. 1). Postganglionic neurons of the gastric parasympathetic system are located mainly in the myenteric and submucosal plexuses of the enteric nervous system, with the parasympathetic ganglia shown in FIG. 1 to be attached to the enteric nervous system, within the wall of the gut. Thus, on reaching the enteric plexuses, individual vagal axons ramify extensively and widely, contacting large numbers of enteric neurons [POWLEY T L. Vagal input to the enteric nervous system. Gut 47 (2000) Suppl 4:iv30-2]. Stimulation of these parasympathetic nerve fibers generally causes an increase in activity of the entire enteric nervous system, which in turn enhances activity of most gastric functions, owing to the fact that the parasympathetic neurotransmitter acetylcholine generally excites gastric activity. However, the parasympathetic efferent fibers may also inhibit activity as follows. Vagal preganglionic efferents to the stomach that excite or inhibit smooth muscle contraction form two pathways. First, there is an excitatory pathway with cholinergic preganglionic neurons from the rostral dorsal motor nucleus and cholinergic postganglionic neurons in the enteric ganglia (transmitters Ach or Substance P). Second, there is an inhibitory pathway with cholinergic preganglionic neurons from the caudal dorsal motor nucleus and nitrergic postganglionic neurons in the enteric ganglia (transmitters nitric oxide, VIP, or ATP). These excitatory and inhibitory pathways also regulate the activity of interstitial cells of Cajal, which in turn modulate the contraction of smooth muscle cells. Thus, vagal efferents may either contract or relax gastric smooth muscle, depending on the selective stimulation of particular excitatory or inhibitory fibers that originate in particular locations of the dorsal motor nucleus [CHANG H Y, Mashimo H, Goyal R K. Musings on the wanderer: what's new in our understanding of vago-vagal reflex? IV. Current concepts of vagal efferent projections to the gut. Am J Physiol Gastrointest Liver Physiol 284(3, 2003):G357-G366; PAGANI F D, Norman W P, Kasbekar D K, Gillis R A. Localization of sites within dorsal motor nucleus of vagus that affect gastric motility. Am J Physiol 249(1 Pt 1, 1985):G73-G84].

So-called vago-vagal reflex circuits cause smooth muscle of the stomach to contract or relax in response to afferent sensory signals that are sent from the stomach and other portions of the gastrointestinal tract. The circuits are comprised of sensory afferent fibers whose terminals impinge on nucleus tractus solitarius (NTS) neurons, which project to dorsal motor nucleus (DMV) cells, which in turn provide the preganglionic efferent fibers controlling excitatory and inhibitory postganglionic cells. The strategic location outside the blood-brain barrier of vago-vagal circuits, including the area postrema, makes them accessible to circulating hormones, cytokines, and chemokines that can dramatically alter vago-vagal reflex responsiveness [TRAVAGLI R A, Hermann G E, Browning K N, Rogers R C. Musings on the wanderer: what's new in our understanding of vago-vagal reflexes? III. Activity-dependent plasticity in vago-vagal reflexes controlling the stomach. Am J Physiol Gastrointest Liver Physiol 284(2, 2003):G180-G187; Richard A. GILLIS, John A. Quest, Francis D. Pagani, Wesley P. Norman. Control centers in the central nervous system for regulating gastrointestinal motility. Compr Physiol 2011, Supplement 16: Handbook of Physiology, The Gastrointestinal System, Motility and Circulation: 621-683 (first published 1989); TRAVAGLI R A, Hermann G E, Browning K N, Rogers R C. Brainstem circuits regulating gastric function. Annu Rev Physiol 68 (2006):279-305; BROWNING K N, Travagli R A. Plasticity of vagal brainstem circuits in the control of gastric function. Neurogastroenterol Motil 22(11, 2010):1154-63].

Vagal activation during meals starts when thought, sight, smell and taste of food stimulate gastrointestinal secretion, motility and hormone release. Subsequently, vago-vagal reflexes, elicited by the distension of the esophagus and the stomach, induce antral contractions and receptive and adaptive relaxation of the proximal stomach, ensuring gastric accommodation to the meal. The motor responses of the proximal stomach are then mediated by complex, partly antagonistic vagal pathways. There may be three possible mechanisms of gastric dysfunction in patients with functional dyspepsia, all of which may involve the vagus nerve: (i) delayed gastric emptying as in gastroparesis, (ii) impaired gastric accommodation of food intake, and (iii) hypersensitivity to gastric distention.

Sympathetic gastric fibers originate in celiac sympathetic ganglia and terminate mainly on the enteric plexuses, but a few nerves terminate in the mucosa itself. Messenger molecules mediate input to the ganglia and modulate sympathetic efferent output, for example, the hormone leptin and carbon monoxide, which is synthesized by heme oxygenase 2. The sympathetic fibers tend to course beside blood vessels (BV in FIG. 1). Their stimulation generally inhibits activity of the stomach, primarily by inhibiting action in the enteric plexuses. Sympapthetic efferents innervate both precapillary and postcapillary blood vessels in the stomach and modulate gastric blood flow, in conjunction with the enteric nerves. Sympathetic regulation of motility primarily involves inhibitory presynaptic modulation of vagal cholinergic input to postganglionic neurons in the enteric plexus [O LUNDGREN. Sympathetic input into the enteric nervous system. Gut 47(Suppl IV, 2000):iv33-iv35; LOMAX A E, Sharkey K A, Furness J B. The participation of the sympathetic innervation of the gastrointestinal tract in disease states. Neurogastroenterol Motil 22(1, 2010):7-18].

Stomach muscle contractions occur rhythmically, due to so-called "slow waves" of smooth muscle membrane potential. The slow waves are caused by interactions among the gastric smooth muscle cells (SM in FIG. 1) and networks of interstitial cells of Cajal (ICC, see FIG. 1). These interstitial cells undergo spontaneous cyclic changes in membrane potential and act as electrical pacemakers for the gastric smooth muscle cells. The slow waves may result in muscle contraction in the stomach, and they may also produce spike potentials that in turn cause muscle contraction. Electrical signals that initiate muscle contractions travel from one muscle fiber to adjacent muscle fibers via gap junctions [MOSTAFA R M, Moustafa Y M, Hamdy H. Interstitial cells of Cajal, the Maestro in health and disease. World J Gastroenterol 16(26, 2010):3239-3248].

There are multiple subtypes of ICC cells, including those that form networks in the myenteric plexus (ICC-MY cells) and those in intramuscular networks (ICC-IM cells). Both ICC-MY and ICC-IM are likely to serve a major role in slow wave generation and propagation. As described below, the ICC-IM are particularly relevant to the present invention because vagal gastrointestinal mechanoreceptors at the smooth muscle endings of vagus afferent nerves, known as intramuscular arrays (IMA, see FIG. 1), form substantial contacts with interstitial cells of Cajal of the intramuscular type (ICC-IM) [Dirk F .van HELDEN, Derek R. Layer, John Holdsworth and Mohammad S. Imtiaz. The generation and propagation of gastric slow waves. Proceedings of the Australian Physiological Society 40 (2009): 109-120; POWLEY T L, Wang X Y, Fox E A, Phillips R J, Liu L W, Huizing a J D. Ultrastructural evidence for communication between intramuscular vagal mechanoreceptors and interstitial cells of Cajal in the rat fundus. Neurogastroenterol Motil 20(1, 2008): 69-79].

FIG. 1 shows smooth muscle cells (SM) in contact with a network of interstitial cells of Cajal (ICC network), which in turn lies adjacent to motor neurons of the enteric nervous system. These three structures constitute a gastrointestinal neuromuscular junction, in which enteric motor neurons stimulate or inhibit contraction of the smooth muscle cells, with the ICC serving as an intermediary. When action potentials invade varicosities of the enteric motor neurons, stored transmitters are released (ATP and VIP for inhibitory neurons and ACh and SP for excitatory neurons), and enzymes responsible for de novo transmitters are activated. In particular, in inhibitory enteric motor neurons, NO is made by Ca-dependent activation of nitric oxide synthase—NOS). The close apposition between varicose nerve terminals and ICC facilitate rapid diffusion to receptors expressed by ICC. ICC are electrically coupled to smooth muscle via gap junctions, and electrical responses elicited in ICC are conveyed to smooth muscle cells via electrical conduction. In the smooth muscle cells, excitatory depolarization responses enhance excitability and increase Ca influx, or inhibitory hyperpolarization responses reduce excitability and block contraction [Alan J. BURNS, Alan E. J. Lomax, Shigeko Torihashi, Kenton M. Sanders, and Sean M. Ward. Interstitial cells of Cajal mediate inhibitory neurotransmission in the stomach. Proc. Natl. Acad. Sci. USA 93 (1996):12008-12013; S WARD. Interstitial cells of Cajal in enteric neurotransmission. Gut 47(Suppl 4, 2000): iv40-iv43; WARD S M, Sanders K M. Interstitial cells of Cajal: primary targets of enteric motor innervation. The Anatomical Record 262(1, 2001):125-135; Satoshi IINO and Kazuhide Horiguchi. Interstitial Cells of Cajal Are Involved in Neurotransmission in the Gastrointestinal Tract. Acta Histochem Cytochem 39(6, 2006): 145-153].

The neurotransmitter receptors are also expressed by smooth muscle cells, and they may also be used without intermediation by the ICC. That is to say, neuromuscular activation or inhibition may also be between enteric motor neurons and smooth muscle cells alone [HUIZINGA J D, Liu L W, Fitzpatrick A, White E, Gill S, Wang X Y, Zarate N, Krebs L, Choi C, Starret T, Dixit D, Ye J. Deficiency of intramuscular ICC increases fundic muscle excitability but does not impede nitrergic innervation. Am J Physiol Gastrointest Liver Physiol 294(2, 2008): G589-G594; GOYAL R K, Chaudhury A. Mounting evidence against the role of ICC in neurotransmission to smooth muscle in the gut. Am J Physiol Gastrointest Liver Physiol 298(1, 2010):G10-G3]. However, if mature and functional ICC are not present in the neuromuscular junction of stomach muscle, neuromuscular transmission may be suboptimal or dysfunctional, leading to gastric mobility problems.

In fact, loss of ICC is the single most common pathophysiological feature found in patients with gastroparesis, and it is commonly observed in gastroparetic animal models as well [GROVER M, Farrugia G, Lurken M S, et al. Cellular changes in diabetic and idiopathic gastroparesis. Gastroenterology 140(5, 2011):1575-1585; Harsha VITTAL, Gianrico Farrugia, Guillermo Gomez and Pankaj J. Pasricha. Mechanisms of Disease: the pathological basis of gastroparesis—a review of experimental and clinical studies. Nat Clin Pract Gastroenterol Hepatol 4(6, 2007):336-346; ZARATE N, Mearin F, Wang X Y, Hewlett B, Huizing a J D, Malagelada J R. Severe idiopathic gastroparesis due to neuronal and interstitial cells of Cajal degeneration: pathological findings and management. Gut 52(7, 2003):966-70; BATTAGLIA E, Bassotti G, Bellone G, Dughera L, Serra A M, Chiusa L, Repici A, Mioli P, Emanuelli G. Loss of interstitial cells of Cajal network in severe idiopathic gastroparesis. World J Gastroenterol 12(38, 2006):6172-6177; FORSTER J, Damjanov I, Lin Z, Sarosiek I, Wetzel P, McCallum R W. Absence of the interstitial cells of Cajal in patients with gastroparesis and correlation with clinical findings. J Gastrointest Surg 9(1, 2005):102-108; LIN Z, Sarosiek I, Forster J, Damjanov I, Hou Q, McCallum R W. Association of the status of interstitial cells of Cajal and electrogastrogram parameters, gastric emptying and symptoms in patients with gastroparesis. Neurogastroenterol Motil 22(1, 2010):56-61; WANG X Y, Huizing a J D, Diamond J, Liu L W. Loss of intramuscular and submuscular interstitial cells of Cajal and associated enteric nerves is related to decreased gastric emptying in streptozotocin-induced diabetes. Neurogastroenterol Motil 21(10, 2009): 1095-e92; ORDOG T, Takayama I, Cheung W K, Ward S M, Sanders K M. Remodeling of networks of interstitial cells of Cajal in a murine model of diabetic gastroparesis. Diabetes 49(10, 2010):1731-1739].

ICC injury may be due to a deficiency of growth factors necessary for normal ICC survival. For example, in diabetes, defective insulin and insulin-like growth factor I (IGF-I) pathways are thought to lead to ICC depletion. ICC injury seems to have gradations: structural injury to ICC without loss of ICC, followed by a reduction in the density of the networks of ICC with preservation of some function, followed by more severe loss up to complete loss of function. When the ICC are lost, the cells may not actually die, but may instead dedifferentiate into cells having smooth muscle and fibroblast features. The process may also be reversible, wherein such un- or de-differentiated cells become mature ICC after the appropriate trophic factors are supplied [HUIZINGA J D, White E J. Progenitor cells of interstitial cells of Cajal: on the road to tissue repair. Gastroenterology 134(4, 2008):1252-1254; MEI F, Yu B, Ma H, Zhang H J, Zhou D S. Interstitial cells of Cajal could regenerate and restore their normal distribution after disrupted by intestinal transection and anastomosis in the adult guinea pigs. Virchows Arch 449(3, 2006):348-57; LORINCZ A, Redelman D, Horváth V J, Bardsley M R, Chen H, Ordög T. Progenitors of interstitial cells of cajal in the postnatal murine stomach. Gastroenterology 134(4, 2008): 1083-1093].

Therefore, it is one objective of the present invention to provide requisite trophic factors to gastric ICC cells and their progenitors, through electrical stimulation of the vagus nerve. Certain ICC are known to require functionally intact innervation by the vagus nerve, otherwise the ICC will be damaged or lost. Such ICC are found in association with intramuscular arrays (IMA, see FIG. 1). The IMA are vagal mechanoreceptors, consisting of arrays of parallel telodendria running in close proximity to one another and to muscle fibers. They send afferent mechanical information via vagal nerves, apparently serving much the same type of function as skeletal muscle spindles. IMAs lie in close association not only with ICCs, but also with other afferent and efferent axons, presumed to be enteric neurons, that conceivably use transduced signals from the IMAs in the performance of feedback loops that tune the mechanical responses to IMAs dynamically (see FIG. 1) [POWLEY T L, Phillips R J. Vagal intramuscular array afferents form complexes with interstitial cells of Cajal in gastrointestinal smooth muscle: analogues of muscle spindle organs? Neuroscience 186 (2011):188-200; POWLEY T L, Wang X Y, Fox E A, Phillips R J, Liu L W, Huizing a J D. Ultrastructural evidence for communication between intramuscular vagal mechanoreceptors and interstitial cells of Cajal in the rat fundus. Neurogastroenterol Motil 20(1, 2008): 69-79].

When vagal afferents are deliberately damaged by injections into the nodose ganglion, degeneration of ICCs associated with IMAs occurs shortly thereafter [HUIZINGA J D, Reed D E, Berezin I, Wang X Y, Valdez D T, Liu L W, Diamant N E. Survival dependency of intramuscular ICC on vagal afferent nerves in the cat esophagus. Am J Physiol Regul Integr Comp Physiol 294(2, 2008):R302-R310]. This indicates that the vagus afferent is not only serving as an afferent transmitter of information about the mechanical state in the vicinity of the IMA, but is also responsible in part for maintaining the functional and structural integrity of ICCs. That is to say, the vagal afferent nerve appears to be providing factors necessary for the maintenance of ICCs. In that regard, it is well established that gastrointestinal vagal afferents subserve an efferent role by release of neurotransmitters or other factors from their varicose nerve terminals [RAYBOULD H E. The future of GI and liver research: editorial perspectives. IV. Visceral afferents: an update. Am J Physiol Gastrointest Liver Physiol 284(6, 2003):G880-G882]. Even some putative gastric afferents derived from dorsal root ganglia behave as though they were efferent nerves [HOLZER P, Maggi C A. Dissociation of dorsal root ganglion neurons into afferent and efferent-like neurons. Neuroscience 86(2, 1998):389-398].

Interaction between nerves and muscles can be considered at two levels: short-term interaction (or neurotransmission) that takes seconds or less, and long-term interaction that concerns development and takes longer, sometimes days. The line between these is not distinct and there are semantic problems in defining neurotransmitters, neuromodulators, neurohormones, second messengers and trophic factors. So, for want of a better term, the factors that are provided by the vagus afferent to promote ICC maintenance are labeled in FIG. 1 as "trophic factor". The identity of the trophic factor(s) at the IMA is not known, although Stem Cell Factor (also known as SCF, kit-ligand, KL, or steel factor) has a well known role in the maturation and maintenance of ICC, and the vagus afferent could either provide SCF itself, or produce trophic effects on adjacent smooth muscle cells or neighboring enteric neurons, causing them to provide sufficient quantities of SCF to the ICC (or other such trophic factors, e.g., involving nNOS and nitric oxide) [LORINCZ A, Redelman D, Horváth V J, Bardsley M R, Chen H, Ordög T. Progenitors of interstitial cells of cajal in the postnatal murine stomach. Gastroenterology 134(4, 2008):1083-1093; TORIHASH I S, Yoshida H, Nishikawa S, Kunisada T, Sanders K M. Enteric neurons express Steel factor-lacZ transgene in the murine gastrointestinal tract. Brain Res 738(2, 1996):323-328].

In the gastroparetic patient, the ICC may have become damaged by a variety of mechanisms, and the corresponding IMA therefore will not be transmitting normal vagal afferent signals. In particular, the smooth muscle in the absence of ICC might have increased excitability, such that vagal afferent signals from the IMA are abnormal [HUIZINGA J D, Liu L W, Fitzpatrick A, White E, Gill S, Wang X Y, Zarate N, Krebs L, Choi C, Starret T, Dixit D, Ye J. Deficiency of intramuscular ICC increases fundic muscle excitability but does not impede nitrergic innervation. Am J Physiol Gastrointest Liver Physiol 294(2, 2008): G589-G594]. An objective of the invention is to electrically stimulate the vagus afferent nerve so as to imitate signals that would normally have been transmitted by the vagal afferents, such that the vagus nerve will respond by providing to the damaged ICC what would have been the normal trophic factors. This will thereby reverse ICC damage, and as a consequence improve gastric motility. Thus, one aspect of the invention is to electrical stimulate the vagal afferents in such a way as to signal to cell nuclei within the nodose ganglion that the ICC-associated mechanoreceptors are active normally (even though they are not) and respond accordingly to produce and transport the normal trophic factors. To the extent that the vagal afferent signals without externally applied electrical stimulation are sensed as being nociceptive, imposition of the externally applied normal signal will also relieve unpleasant sensations.

Such stimulation of the afferent vagus nerve over a short period of time will not necessarily have a long-lasting therapeutic effect, even taking into account the time needed for the resulting trophic factors to reverse ICC damage. Instead, according to the present invention, restored gastric mobility may occur more or less abruptly after a protocol of vagus nerve stimulation treatment over a period of days or weeks, for the following reasons. Individual interstitial cells of Cajal of both the ICC-IM and ICC-MY types are intrinsically rhythmic and act as pacemakers for waves of contraction [Dirk F. van HELDEN, Derek R. Layer, John Holdsworth and Mohammad S. Imtiaz. The generation and propagation of gastric slow waves. Proceedings of the Australian Physiological Society 40 (2009): 109-120]. The cells' rhythms are not independent of one another, however, because they are mechanically and electrically coupled with one another, at a minimum through enteric nerves and intervening smooth muscle. Therefore the cells within a network of interstitial cells of Cajal may be regarded as a set of semi-autonomous oscillators, coupled to one another.

Local mechanical oscillations of the stomach would damp themselves out through friction, were they not sustained by a source of metabolic energy, i.e., the equation describing the oscillation will generally be non-conservative. Furthermore, because the velocities of displacement of muscle segments relative to their average or resting position are generally not linearly proportional to the displacements themselves, because the period of oscillation may be a function of the oscillation amplitude rather than a simple constant, and because the tension and compression that segments exert upon one another are likewise generally more complicated than a simple spring constant, then equations that characterize the oscillators and their interactions must generally be non-linear. The properties of such non-linear oscillators are currently understood through the analysis of non-linear differential equation prototypes, such as Van der Pol, FitzHugh-Nagumo, Morris-Lecar, Ellias-Grossberg, and Stuart-Landau equations.

Although the detailed oscillations described by such prototypical equations are dependent on the detailed form of the equations, the qualitative behaviors of such non-linear coupled oscillator equations may often be understood independently of the particular form of the non-linear equation. For example, it is well understood in general that non-linear oscillators, including a set of coupled non-linear oscillators, may exhibit qualitatively different behaviors when the parameters of their equations lie within certain bounds. When graphs are drawn showing the value of one parameter on one axis, and the value of another parameter on another axis, regions of this parameter space may be circumscribed to show what sets of parameter values correspond to each type of qualitatively different dynamics, i.e, a phase diagram. Examples of such phase diagrams, which are given by MATTHEWS and colleagues, circumscribe different regions of phase space having qualitatively different dynamics [Paul C. MATTHEWS and Steven H. Strogatz. Phase diagram for the collective behavior of limit-cycle oscillators. Phys. Rev. Lett. 65 (1990): 1701-1704; Paul C. MATTHEWS and Steven H. Strogatz. Phase diagram for the collective behavior of limit-cycle oscillators. Phys. Rev. Lett. 65 (1990): 1701-1704; Paul C. MATTHEWS, Renato E. Mirollo, and Steven H. Strogatz. Dynamics of a large system of coupled nonlinear oscillators. Physica D: Nonlinear Phenomena 52 (2-3, 1991): 293-331]. According to the present invention, a patient with gastroparesis has a stomach with ICC that are trapped in a region of phase space in which gastric emptying dynamics is abnormal. An objective of the invention is to move the system of coupled non-linear oscillators (ICC network) into a region of phase space corresponding to more nearly normal gastric emptying. When doing so, there may be an abrupt change in physiological dynamics, as the system passes the boundary from one qualitatively different dynamical region in phase space to another.

When one or more of the parameters of the set of coupled nonlinear oscillators may be varied under external influences to produce qualitative changes of phase in the system, the parameter is said to be an order parameter. When a network of interstitial cells of Cajal are represented mathematically as nonlinear oscillators that are coupled to one another, an order parameter for the system may be, for example, the volume of food in the stomach. Another order parameter can be related to the magnitude and duration of vagus nerve stimulation. For example, let the accumulated "Vagus Nerve stimulation" with a particular stimulation waveform be denoted as S(t), which may for illustration purposes be represented as one that increases at a rate proportional to the stimulation voltage V and decays with a time constant $\tau_P$, such that after prolonged stimulation, the accumulated stimulation effectiveness will saturate at a value equal to the product of V and $\tau_P$. Thus, if $T_P$ is the duration of a stimulus pulse, then for time t<$T_P$, S(t)=$V\tau_P[1-\exp(-t/\tau_P)]+S_0 \exp(-t/\tau_P)$, and for t>$T_P$, S(t)=S($T_P$) $\exp(-[t-T_P]/\tau_P)$ where the time t is measured from the start of a pulse, and $S_0$ is the value of S when t=0. Then, as stimuli to the vagus nerve are applied, the value of S will change to move the system within phase space. It may therefore be possible for the system to switch from one dynamical phase to another, even if the stomach had a constant volume (or other such order parameter was constant). Therefore, treatment over an extended period of time by vagus nerve stimulation may be required in order to achieve the objective of changing the qualitative dynamics of the network of interstitial cells of Cajal, by moving the system into a more normal region of phase space. This may involve adaptive changes in the above-mentioned vago-vagal reflexes, which also couple interstitial cells of Cajal to one another.

A disclosure similar to the foregoing was made by Applicants in connection with the treatment bladder smooth muscle motility disorders, in commonly assigned co-pending patent application US20120101326, entitled Non-invasive electrical and magnetic nerve stimulators used to treat overactive bladder and urinary incontinence, to SIMON et al., which is hereby incorporated by reference. It is understood that nonlinear coupled oscillator equations describing gastric emptying (rather than bladder emptying) may be constructed by adapting previously described models of stomach dynamics [DU P, O'Grady G, Gibbons S J, Yassi R, Lees-Green R, Farrugia G, Cheng L K, Pullan A J. Tissue-specific mathematical models of slow wave entrainment in wild-type and 5-HT(2B) knockout mice with altered interstitial cells of Cajal networks. Biophys J 98(9, 2010):1772-1781; LEES-GREEN R, Du P, O'Grady G, Beyder A, Farrugia G, Pullan A J. Biophysically based modeling of the interstitial cells of cajal: current status and future perspectives. Front Physiol 2 (2011):29, pp. 1-19].

Gastroparesis and functional dyspepsia are accompanied by abnormal interoception and visceral hypersensitivity. Many neural circuits that are involved in interoception are located in higher regions of the central nervous system, and a further objective of the invention is to electrically stimulate the vagus nerve in such a way as to modulate the activity of those neural circuits. They are also shown in of FIG. 1 and described in paragraphs that follow [CRAIG A D. How do you feel? Interoception: the sense of the physiological condition of the body. Nat Rev Neurosci 3(8, 2002):655-666; BIELEFELDT K, Christianson J A, Davis B M. Basic and clinical aspects of visceral sensation: transmission in the CNS. Neurogastroenterol Motil 17(4, 2005):488-499; MAYER E A, Naliboff B D, Craig A D. Neuroimaging of the brain-gut axis: from basic understanding to treatment of functional GI disorders. Gastroenterology 131(6, 2006):1925-1942].

Sensations of gastrointestinal pain and unpleasantness (e.g. nausea and early satiety) arise from signals sent by parasympathetic and sympathetic afferent nerves. The latter are considered to be the primary culprit for pain, but as described below, parasympathetic afferents also contribute [M KOLLARIK, F Ru and M Brozmanova. Vagal afferent nerves with the properties of nociceptors. Auton Neurosci 153(1-2, 2010): 12, pp. 1-20]. Among afferents whose cell bodies are found in the dorsal root ganglia, the ones having type B cell bodies are most significant (see FIG. 1). They terminate in lamina I of the spinal and trigeminal dorsal horns, which for stomach afferents correspond largely to spinal levels T6-T9. Other afferent nerves that terminate in the deep dorsal horn provide signals related to mechanoreceptive, proprioceptive and nociceptive activity (not shown), but in general they are not responsible for unpleasant sensations.

Lamina I neurons project to many locations. First, they project to the sympathetic regions in the intermediomedial and intermediolateral cell columns of the thoracolumbar cord, where the sympathetic preganglionic cells of the autonomic nervous system originate (See FIG. 1). For gastric sympathetic nerves, the preganglionic nerves project to the celiac ganglia, from which the postgangionic efferent nerves innervating the stomach wall and gastric blood vessels arise.

Second, in the medulla, lamina I neurons project to the A1 catecholaminergic cell groups of the ventrolateral medulla and then to sites in the rostral ventrolateral medulla (RVLM) which is interconnected with the sympathetic neurons that project to spinal levels. Only a limited number of discrete regions within the supraspinal central nervous system project to sympathetic preganglionic neurons in the intermediolateral column (see FIG. 1). The most important of these regions are the rostral ventral lateral medulla (RVLM), the rostral ventromedial medulla (RVMM), the midline raphe, the paraventricular nucleus (PVN) of the hypothalamus, the medullocervical caudal pressor area (mCPA), and the A5 cell group of the pons. The first four of these connections to the intermediolateral nucleus are shown in FIG. 1 [STRACK A M, Sawyer W B, Hughes J H, Platt K B, Loewy A D. A general pattern of CNS innervation of the sympathetic outflow demonstrated by transneuronal pseudorabies viral infections. Brain Res. 491 (1, 1989): 156-162].

The rostral ventral lateral medulla (RVLM) is the primary regulator of the sympathetic nervous system, sending excitatory fibers (glutamatergic) to the sympathetic preganglionic neurons located in the intermediolateral nucleus of the spinal cord. Vagal afferents synapse in the NTS, and their projections reach the RVLM via the caudal ventrolateral medulla. However, resting sympathetic tone also comes from sources above the pons, from hypothalamic nuclei, various hindbrain and midbrain structures, as well as the forebrain and cerebellum, which synapse in the RVLM. Only the hypothalamic projection to the RVLM is shown in FIG. 1.

The RVLM shares its role as a primary regulator of the sympathetic nervous system with the rostral ventromedial medulla (RVMM) and medullary raphe. Differences in function between the RVLM versus RVMM/medullary raphe have been elucidated for cardiovascular control, but are not well characterized for gastrointestinal control. Differential control of the RVLM by the hypothalamus may also occur via circulating hormones such as vasopressin. The RVMM contains at least three populations of nitric oxide synthase neurons that send axons to innervate functionally similar sites in the NTS and nucleus ambiguus. Circuits connecting the RVMM and RVLM may be secondary, via the NTS and hypothalamus.

In the medulla, lamina I neurons also project another site, namely, to the A2 cell group of the nucleus of the solitary tract, which also receives direct parasympathetic (vagal and glossopharyngeal) afferent input. As indicated above, the nucleus of the solitary tract projects to many locations, including the parabrachial nucleus. In the pons and mesencephalon, lamina I neurons project to the periaqueductal grey (PAG), the main homeostatic brainstem motor site, and to the parabrachial nucleus. Sympathetic and parasympathetic afferent activity is integrated in the parabrachial nucleus. It in turn projects to the insular cortex by way of the ventromedial thalamic nucleus (VMb, also known as VPMpc). A direct projection from lamina I to the ventromedial nucleus (VMpo), and a direct projection from the nucleus tractus solitarius to the VMb, provide a rostrocaudally contiguous column that represents all contralateral homeostatic afferent input. They project topographically to the mid/posterior dorsal insula (See FIG. 1).

In humans, this cortical image is re-represented in the anterior insula on the same side of the brain. The parasympathetic activity is re-represented in the left (dominant) hemisphere, whereas the sympathetic activity is re-represented in the right (non-dominant) hemisphere. These re-representations provide the foundation for a subjective evaluation of interoceptive state, which is forwarded to the orbitofrontal cortex (See FIG. 1).

The right anterior insula is associated with subjective awareness of homeostatic emotions (e.g., visceral and somatic pain, temperature, sexual arousal, hunger, and thirst) as well as all emotions (e.g., anger, fear, disgust, sadness, happiness, trust, love, empathy, social exclusion). This region is intimately interconnected with the anterior cingulate cortex (ACC). The unpleasantness of pain is directly correlated with ACC activation. The anterior cingulate cortex and insula are both strongly interconnected with the orbitofrontal cortex, amygdala, hypothalamus, and brainstem homeostatic regions, of which only a few connections are shown in FIG. 1.

Visceral pain and hypersensitivity is a characteristic feature in patients with FGID such as functional dyspepsia. In view of FIG. 1, the pathophysiological basis of hypersensitivity may be a combination of sensitized visceral afferent pathways (enteric, parasympathetic, sympathetic), alterations in cortical processing of visceral afferent inputs, and changes in descending modulatory inputs from the brainstem to the spinal cord, and to enteric neurones via the vagus nerve. The relative contributions of particular ascending and descending pathways are likely to vary from patient to patient [ANAND P, Aziz Q, Willert R, van Oudenhove L. Peripheral and central mechanisms of visceral sensitization in man. Neurogastroenterol Motil 19(1 Suppl, 2007):29-46; Clive H WILDER-SMITH. The balancing act: endogenous modulation of pain in functional gastrointestinal disorders. Gut 60 (2011):1589-1599].

Methods of the present invention comprise modulation of two target regions using vagus nerve stimulation to reduce visceral pain, unpleasantness, and hypersensitivity. A first method targets the front end of the interoceptive pathways shown in FIG. 1 (nucleus tractus solitarius, area postrema, and dorsal motor nucleus). A second method targets the distal end of the interoceptive pathways (anterior insula and anterior cingulate cortex).

According to the first method, electrical stimulation of A and B fibers alone of a vagus nerve causes increased inhibitory neurotransmitters in the brainstem, which in turn inhibits signals sent to the parabrachial nucleus, VMb and VMpo. The stimulation uses special devices and a special waveform (described below), which minimize effects involving C fibers that might produce unwanted side-effects. The electrical stimulation first affects the dorsal vagal complex, which is the major termination site of vagal afferent nerve fibers. The dorsal vagal complex consists of the area postrema (AP), the nucleus of the solitary tract (NTS) and the dorsal motor nucleus of the vagus. The AP projects to the NTS and dorsal motor nucleus of the vagus bilaterally. It also projects bilaterally to the parabrachial nucleus and receives direct afferent input from the vagus nerve. Thus, the area postrema is in a unique position to receive and modulate ascending interoceptive information and to influence autonomic outflow [PRICE C J, Hoyda T D, Ferguson A V. The area postrema: a brain monitor and integrator of systemic autonomic state. Neuroscientist 14(2, 2008):182-194].

The area postrema (AP) is well known as the medullary structure in the brain that controls vomiting, but it may play a more general role in mediating introceptive sensations, comprising not only vomiting, but also such sensations as postprandial fullness, bloating, pain, and nausea. It is able to play this role because of its ability to sense circulating hormones and other soluble physiologically active factors, such as toxins. It is heavily vascularized, and by virtue of its lack of tight junctions between endothelial cells and the presence of fenestrated capillaries, peptide and other physiological signals borne in the blood have direct access to its neurons that project to the NTS, dorsal motor nucleus and parabrachial nucleus. This includes hormones that are secreted before and after ingesting a meal, such as gherlin and cholecystokinin. An addition, the AP receives direct afferent input from the vagus nerve, including afferents from the stomach.

Excitatory nerves within the dorsal vagal complex generally use glutamate as their neurotransmitter. To inhibit neurotransmission within the dorsal vagal complex, the present invention makes use of the bidirectional connections that the NTS has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are described below. Thus, acting in opposition to glutamate-mediated (and possibly substance P) activation of the AP and dorsal motor nucleus by the NTS are GABA, and/or serotonin, and/or norepinephrine from the periaqueductal gray, raphe nucei, and locus coeruleus, respectively. FIG. 1 shows how those excitatory and inhibitory influences combine to modulate the output of the dorsal motor nucleus. Similar influences combine within the NTS itself, and the combined inhibitory influences on the NTS and dorsal motor nucleus produce an inhibitory effect on the AP through their efferent projections to the AP. The combined inhibitory effects on the NTS and AP thereby inhibit the signals projected to the parabrachial nucleus, VMb and VMpo, thus inhibiting unpleasant interoceptive sensations.

The activation of inhibitory circuits in the periaqueductal gray, raphe nucei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1 [PUDOVKINA O L, Cremers T I, Westerink B H. The interaction between the locus coeruleus and dorsal raphe nucleus studied with dual-probe microdialysis. Eur J Pharmacol 7 (2002); 445(1-2):37-42; REICHLING D B, Basbaum A I. Collateralization of periaqueductal gray neurons to forebrain or diencephalon and to the medullary nucleus raphe magnus in the rat. Neuroscience 42(1, 1991): 183-200; BEHBEHANI M M. The role of acetylcholine in the function of the nucleus raphe magnus and in the interaction of this nucleus with the periaqueductal gray. Brain Res 252(2, 1982):299-307].

Projections to and from the locus ceruleus are particularly significant in the present invention because they are also used in the second method that is described below. The vagus nerve transmits information to the locus ceruleus via the nucleus tractus solitarius (NTS), which has a direct projection to the dendritic region of the locus ceruleus. Other afferents to, and efferents from, the locus ceruleus are described by SARA et al, SAMUELS et al, and ASTON-JONES—SARA S J, Bouret S. Orienting and Reorienting: The Locus Coeruleus Mediates Cognition through Arousal. Neuron 76(1, 2012): 130-41; SAMUELS E R, Szabadi E. Functional neuroanatomy of the noradrenergic locus coeruleus: its roles in the regulation of arousal and autonomic function part I: principles of functional organisation. Curr Neuropharmacol 6(3): 235-53; SAMUELS, E. R., and Szabadi, E. Functional neuroanatomy of the noradrenergic locus coeruleus: its roles in the regulation of arousal and autonomic function part II: physiological and pharmacological manipulations and pathological alterations of locus coeruleus activity in humans. Curr. Neuropharmacol. 6 (2008), 254-285; Gary ASTON-JONES. Norepinephrine. Chapter 4 (pp. 47-57) in: Neuropsychopharmacology: The Fifth Generation of Progress (Kenneth L. Davis, Dennis Charney, Joseph T. Coyle, Charles Nemeroff, eds.) Philadelphia: Lippincott Williams & Wilkins, 2002].

In addition to the NTS, the locus ceruleus receives input from the nucleus gigantocellularis and its neighboring nucleus paragigantocellularis, the prepositus hypoglossal nucleus, the paraventricular nucleus of the hypothalamus, Barrington's nucleus, the central nucleus of the amygdala, and prefrontal areas of the cortex. These same nuclei receive input from the NTS, such that stimulation of the vagus nerve may modulate the locus ceruleus via the NTS and a subsequent relay through these structures.

The locus ceruleus has widespread projections throughout the cortex [SAMUELS E R, Szabadi E. Functional neuroanatomy of the noradrenergic locus coeruleus: its roles in the regulation of arousal and autonomic function part I: principles of functional organisation. Curr Neuropharmacol 6 (3):235-53]. It also projects to subcortical regions, notably the raphe nuclei, which release serotonin to the rest of the brain. An increased dorsal raphe nucleus firing rate is thought to be secondary to an initial increased locus ceruleus firing rate from vagus nerve stimulation [Adrienne E. DORR and Guy Debonnelv. Effect of vagus nerve stimulation on serotonergic and noradrenergic transmission. J Pharmacol Exp Ther 318(2, 2006):890-898; MANTA S, Dong J, Debonnel G, Blier P. Enhancement of the function of rat serotonin and norepinephrine neurons by sustained vagus nerve stimulation. J Psychiatry Neurosci 34(4, 2009):272-80]. The locus ceruleus also has projections to autonomic nuclei, including the dorsal motor nucleus of the vagus, as shown in FIG. 1 [FUKUDA, A., Minami, T., Nabekura, J., Oomura, Y. The effects of noradrenaline on neurones in the rat dorsal motor nucleus of the vagus, in vitro. J. Physiol., 393 (1987): 213-231; MARTINEZ-PENA y Valenzuela, I., Rogers, R. C., Hermann, G. E., Travagli, R. A. (2004) Norepinephrine effects on identified neurons of the rat dorsal motor nucleus of the vagus. Am. J. Physiol. Gas-trointest. Liver Physiol., 286, G333-G339; TERHORST, G. J., Toes, G. J., Van Willigen, J. D. Locus coeruleus projections to the dorsal motor vagus nucleus in the rat. Neuroscience, 45 (1991): 153-160].

In another embodiment of the invention, vagus nerve stimulation is used to modulate the activity of particular neural networks known as resting state networks, with the objective of reducing visceral hypersensitivity, pain, or other unpleasant sensations. A neural network is accompanied by oscillations within the network. Low frequency oscillations are likely associated with connectivity at the largest scale of the network, while higher frequencies are exhibited by smaller sub-networks within the larger network, which may be modulated by activity in the slower oscillating larger network. The default network, also called the default mode network (DMN), default state network, or task-negative network, is one such network that is characterized by coherent neuronal oscillations at a rate lower than 0.1 Hz. Other large scale networks also have this slow-wave property, as described below [BUCKNER R L, Andrews-Hanna J R, Schacter D L. The brain's default network: anatomy, function, and relevance to disease. Ann NY Acad Sci 1124 (2008): 1-38; PALVA J M, Palva S. Infra-slow fluctuations in electrophysiological recordings, blood-oxygenation-level-dependent signals, and psychophysical time series. Neuroimage 62(4, 2012):2201-2211; STEYN-ROSS M L, Steyn-Ross D A, Sleigh J W, Wilson M T. A mechanism for ultra-slow oscillations in the cortical default network. Bull Math Biol 73(2, 2011):398-416].

The default mode network corresponds to task-independent introspection (e.g., daydreaming), or self-referential thought. When the DMN is activated, the individual is ordinarily awake and alert, but the DMN may also be active during the early stages of sleep and during conscious sedation. During goal-oriented activity, the DMN is deactivated and one or more of several other networks, so-called task-positive networks (TPN), are activated. DMN activity is attenuated rather than extinguished during the transition between states, and is observed, albeit at lower levels, alongside task-specific activations. Strength of the DMN deactivation appears to be inversely related to the extent to which the task is demanding. Thus, DMN has been described as a task-negative network, given the apparent antagonism between its activation and task performance. The posterior cingulate cortex (PCC) and adjacent precuneus and the medial prefrontal cortex (mPFC) are the two most clearly delineated regions within the DMN [RAICHLE M E, Snyder A Z. A default mode of brain function: a brief history of an evolving idea. Neuroimage 37(4, 2007):1083-1090; BROYD S J, Demanuele C, Debener S, Helps S K, James C J, Sonuga-Barke E J. Default-mode brain dysfunction in mental disorders: a systematic review. Neurosci Biobehav Rev 33(3, 2009):279-96; BUCKNER R L, Andrews-Hanna J R, Schacter D L. The brain's default network: anatomy, function, and relevance to disease. Ann NY Acad Sci 1124 (2008):1-38; BUCKNER R L, Sepulcre J, Talukdar T, Krienen F M, Liu H, Hedden T, Andrews-Hanna J R, Sperling R A, Johnson K A. Cortical hubs revealed by intrinsic functional connectivity: mapping, assessment of stability, and relation to Alzheimer's disease. J Neurosci 29 (2009):1860-1873; GREICIUS M D, Krasnow B, Reiss A L, Menon V. Functional connectivity in the resting brain: a network analysis of the default mode hypothesis. Proc Natl Acad Sci USA 100 (2003): 253-258].

The term low frequency resting state networks (LFRSN or simply RSN) is used to describe both the task-positive and task-negative networks. Using independent component analysis (ICA) and related methods to assess coherence of fMRI Blood Oxygenation Level Dependent Imaging (BOLD) signals in terms of temporal and spatial variation, as well as variations between individuals, low frequency resting state networks in addition to the DMN have been identified, corresponding to different tasks or states of mind. They are related to their underlying anatomical connectivity and replay at rest the patterns of functional activation evoked by the behavioral tasks. That is to say, brain regions that are commonly recruited during a task are anatomically connected and maintain in the resting state (in the absence of any stimulation) a significant degree of temporal coherence in their spontaneous activity, which is what allows them to be identified at rest [SMITH S M, Fox P T, Miller K L, Glahn D C, Fox P M, et al. Correspondence of the brain's functional architecture during activation and rest. Proc Natl Acad Sci USA 106 (2009): 13040-13045].

Frequently reported resting state networks (RSNs), in addition to the DMN, include the sensorimotor RSN, the executive control RSN, up to three visual RSNs, two lateralized fronto-parietal RSNs, the auditory RSN and the temporo-parietal RSN. However, different investigators use different methods to identify the low frequency resting state networks, so different numbers and somewhat different identities of RSNs are reported by different investigators [COLE D M, Smith S M, Beckmann C F. Advances and pitfalls in the analysis and interpretation of resting-state FMRI data. Front Syst Neurosci 4 (2010):8, pp. 1-15]. Examples of RSNs are described in publications cited by COLE and the following: ROSAZZA C, Minati L. Resting-state brain networks: literature review and clinical applications. Neurol Sci 32(5, 2011): 773-85; ZHANG D, Raichle M E. Disease and the brain's dark energy. Nat Rev Neurol 6(1, 2010):15-28; DAMOISEAUX, J. S., Rombouts, S. A. R. B., Barkhof, F., Scheltens, P., Stam, C. J., Smith, S. M., Beckmann, C. F. Consistent resting-state networks across healthy subjects. Proc. Natl. Acad. Sci. U.S.A. 103 (2006): 13848-13853 FOX M D, Snyder A Z, Vincent J L, Corbetta M, Van Essen D C, Raichle M E. The human brain is intrinsically organized into dynamic, anticorrelated functional networks. Proc Natl Acad Sci USA 102 (2005):9673-9678; LI R, Wu X, Chen K, Fleisher A S, Reiman E M, Yao L. Alterations of Directional Connectivity among Resting-State Networks in Alzheimer Disease. AJNR Am J Neuroradiol. 2012 Jul. 12. [Epub ahead of print, pp. 1-6].

For example, the dorsal attention network (DAN) and ventral attention network (VAN) are two networks responsible for attentional processing. The VAN is involved in involuntary actions and exhibits increased activity upon detection of salient targets, especially when they appear in unexpected locations (bottom-up activity, e.g. when an automobile driver unexpectedly senses a hazard or unexpected situation). The DAN is involved in voluntary (top-down) orienting and increases activity after presentation of cues indicating where, when, or to what individuals should direct their attention [FOX M D, Corbetta M, Snyder A Z, Vincent J L, Raichle M E. Spontaneous neuronal activity distinguishes human dorsal and ventral attention systems. Proc Natl Acad Sci USA 103 (2006):10046-10051; WEN X, Yao L, Liu Y, Ding M. Causal interactions in attention networks predict behavioral performance. J Neurosci 32(4, 2012):1284-1292]. The DAN is bilaterally centered in the intraparietal sulcus and the frontal eye field. The VAN is largely right lateralized in the temporal-parietal junction and the ventral frontal cortex. The attention systems (VAN and DAN) have been investigated long before their identification as resting state networks, and functions attributed to the VAN have in the past been attributed to the locus ceruleus/noradrenaline system [ASTON-JONES G, Cohen J D. An integrative theory of locus coeruleus-norepinephrine function: adaptive gain and optimal performance. Annu Rev Neurosci 28 (2005):403-50; BOURET S, Sara S J. Network reset: a simplified overarching theory of locus coeruleus noradrenaline function. Trends Neurosci 28(11, 2005): 574-82; SARA S J, Bouret S. Orienting and Reorienting: The Locus Coeruleus Mediates Cognition through Arousal. Neuron 76(1, 2012):130-41; PETERSEN S E, Posner M I. The attention system of the human brain: 20 years after. Annu Rev Neurosci 35 (2012):73-89; BERRIDGE C W, Waterhouse B D. The locus coeruleus-noradrenergic system: modulation of behavioral state and state-dependent cognitive processes. Brain Res Brain Res Rev 42(1, 2003):33-84].

MENON and colleagues describe the anterior insula as being at the heart of the ventral attention system [ECKERT M A, Menon V, Walczak A, Ahlstrom J, Denslow S, Horwitz A, Dubno J R. At the heart of the ventral attention system: the right anterior insula. Hum Brain Mapp 30(8, 2009):2530-2541; MENON V, Uddin L Q. Saliency, switching, attention and control: a network model of insula function. Brain Struct Funct 214(5-6, 2010):655-667]. SEELEY and colleagues used region-of-interest and independent component analyses of resting-state fMRI data to demonstrate the existence of an independent brain network comprised of both the anterior insula and dorsal ACC, along with subcortical structures including the amygdala, substantia nigra/ventral tegmental area, and thalamus. This network is distinct from the other well-characterized large-scale brain networks, e.g. the default mode network (DMN) [SEELEY W W, Menon V, Schatzberg A F, Keller J, Glover G H, Kenna H, et al. Dissociable intrinsic connectivity networks for salience processing and executive control. J Neurosci 2007; 27(9):2349-2356]. CAUDA and colleagues found that the human insula is functionally involved in two distinct neural networks: i) the anterior pattern is related to the ventralmost anterior insula, and is connected to the rostral anterior cingulate cortex, the middle and inferior frontal cortex, and the temporoparietal cortex; ii) the posterior pattern is associated with the dorsal posterior insula, and is connected to the dorsal-posterior cingulate, sensorimotor, premotor, supplementary motor, temporal cortex, and to some occipital areas [CAUDA F, D'Agata F, Sacco K, Duca S, Geminiani G, Vercelli A. Functional connectivity of the insula in the resting brain. Neuroimage 55(1, 2011):8-23; CAUDA F, Vercelli A. How many clusters in the insular cortex? Cereb Cortex. 2012 Sep. 30. (Epub ahead of print, pp. 1-2)]. TAYLOR and colleagues also report two such resting networks [TAYLOR K S, Seminowicz D A, Davis K D. Two systems of resting state connectivity between the insula and cingulate cortex. Hum Brain Mapp 30(9, 2009):2731-2745]. DEEN and colleagues found three such resting state networks [DEEN B, Pitskel N B, Pelphrey K A. Three systems of insular functional connectivity identified with cluster analysis. Cereb Cortex 21(7, 2011):1498-1506]. The networks involving both the insula and ACC are the ones that are preferably modulated according to the present invention, because they are the ones most associated with pain and the awareness of unpleasant sensations [MALINEN S, Vartiainen N, Hlushchuk Y, Koskinen M, Ramkumar P, Forss N, Kalso E, Hari R. Aberrant temporal and spatial brain activity during rest in patients with chronic pain. Proc Natl Acad Sci USA. 2010 Apr. 6; 107(14, 2010):6493-6497; Nick MEDFORD and Hugo D. Critchley. Conjoint activity of anterior insular and anterior cingulate cortex: awareness and response. Brain Struct Funct 214(5-6, 2010): 535-549].

The present invention modulates the activity of such resting state networks, via the locus ceruleus (or alternatively via another structure that has widespread projections), by electrically stimulating a vagus nerve. Stimulation of a network via the locus ceruleus may activate or deactivate a network, depending on the detailed configuration of adrenergic receptor subtypes within the network and their roles in enhancing or depressing neural activity within the network, as well as subsequent network-to-network interactions. According to the invention, one key to preferential stimulation of a particular resting state network, such as the DMN or those involving the insula and ACC, is to use a vagus nerve stimulation signal that entrains to the signature EEG pattern of that network (see below and MANTINI D, Perrucci M G, Del Gratta C, Romani G L, Corbetta M. Electrophysiological signatures of resting state networks in the human brain. Proc Natl Acad Sci USA 104(32, 2007):13170-13175). By this EEG entrainment method, it may be possible to preferentially attenuate or deactivate the insula/ACC networks in a patient, thereby reducing gastrointestinal pain or other unpleasant sensations. Activation of another network such as the VAN or DMN may also produce the same effect, via network-to-network interactions. Although the locus ceruleus is presumed to project to all of the resting networks, it is thought to project most strongly to the ventral attention network (VAN) [CORBETTA M, Patel G, Shulman G L. The reorienting system of the human brain: from environment to theory of mind. Neuron 58(3, 2008):306-24; MANTINI D, Corbetta M, Perrucci M G, Romani G L, Del Gratta C. Large-scale brain networks account for sustained and transient activity during target detection. Neuroimage 44(1, 2009):265-274]. Thus, deactivation of a particular network may also be attempted by activating another resting state network, because the brain switches between them. Because the vagus nerve stimulation reduces pain by modulating resting state networks via the locus ceruleus, the presently described mechanism differs from previously reported noradrenergic effects, which have nothing to do with resting state networks [PERTOVAARA A. Noradrenergic pain modulation. Prog Neurobiol 80 (2006): 53-83].

Figure 2A:
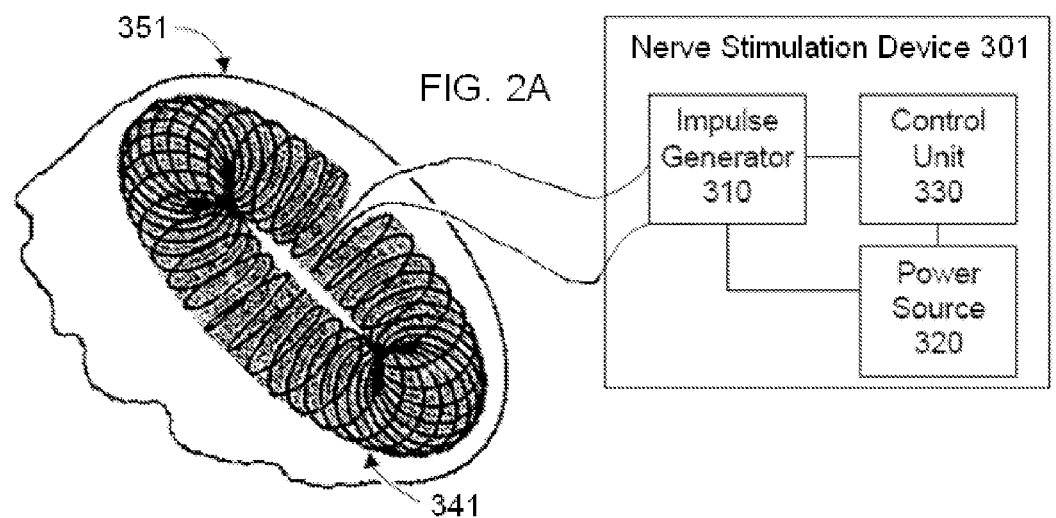
FIG. 2A is a schematic view of a nerve modulating device according to the present invention which supplies controlled pulses of electrical current to a magnetic stimulator coil.

Description of the Magnetic and Electrode-Based Nerve Stimulating/Modulating Devices Devices of the invention that are used to stimulate a vagus nerve will now be described. Either a magnetic stimulation device or an electrode-based device may be used for that purpose. FIG. 2A is a schematic diagram of Applicant's magnetic nerve stimulating/modulating device 301 for delivering impulses of energy to nerves for the treatment of medical conditions such as gastroparesis or functional dyspepsia. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 2A to be a single coil, in practice the coil may also comprise two or more distinct coils, each of which is connected in series or in parallel to the impulse generator 310. Thus, the coil 341 that is shown in FIG. 2A represents all the magnetic stimulator coils of the device collectively. In a preferred embodiment that is discussed below, coil 341 actually contains two coils that may be connected either in series or in parallel to the impulse generator 310.

The item labeled in FIG. 2A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below, the conducting medium with which the coil 341 is in contact need not completely surround the toroid.

The design of the magnetic stimulator 301, which is also adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient, at the site of stimulation on the skin, than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 2B:
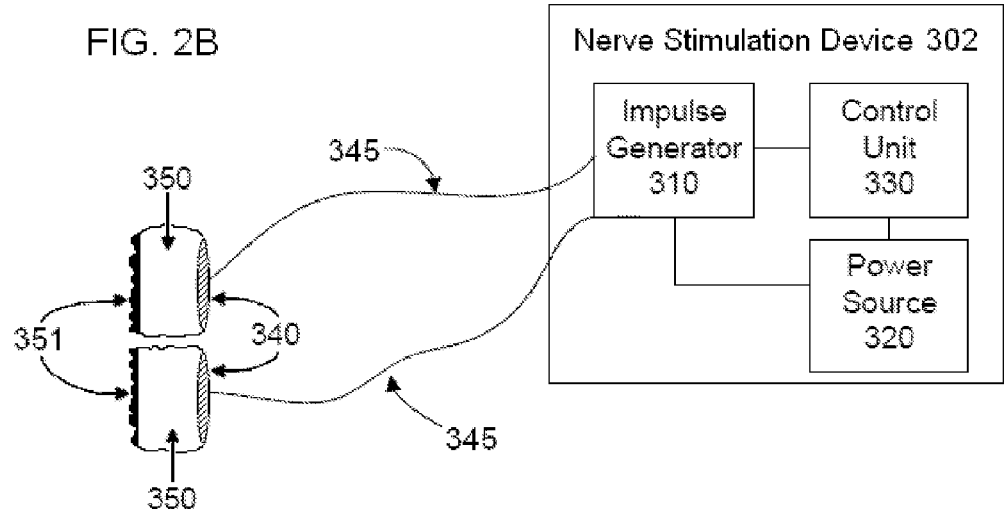
FIG. 2B is a schematic view of a nerve modulating device according to the present invention which supplies controlled pulses of electrical current to surface electrodes.

An alternate embodiment of the present invention is shown in FIG. 2B, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 2B, in practice the electrodes may also comprise three or more distinct electrode elements, each of which is connected in series or in parallel to the impulse generator 310. Thus, the electrodes 340 that are shown in FIG. 2B represent all electrodes of the device collectively.

The item labeled in FIG. 2B as 350 is a volume, contiguous with an electrode 340, that is filled with electrically conducting medium. As described below in connection with particular embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 8), analog-to-digital converters for digitizing externally supplied analog signals (see FIG. 8), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2C:
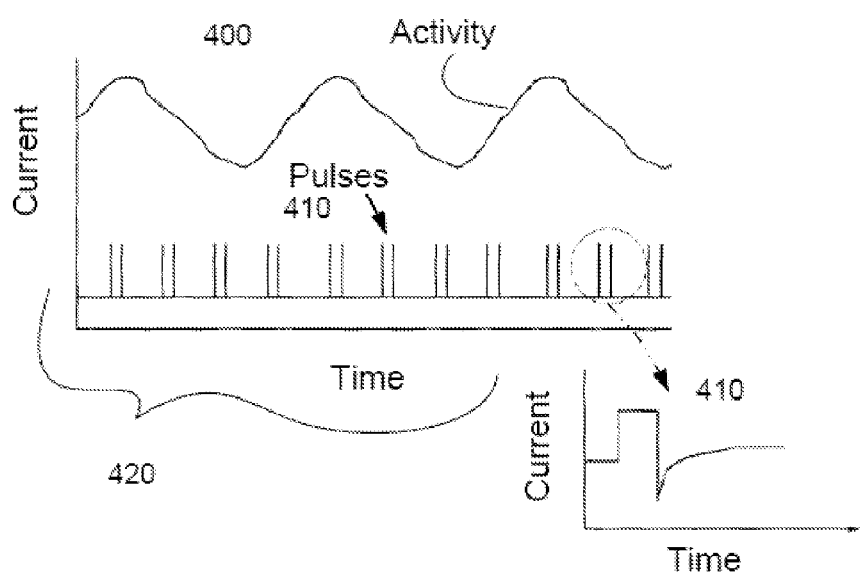
FIG. 2C illustrates an exemplary electrical voltage/current profile for the present invention.

FIG. 2C illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J. Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2D:
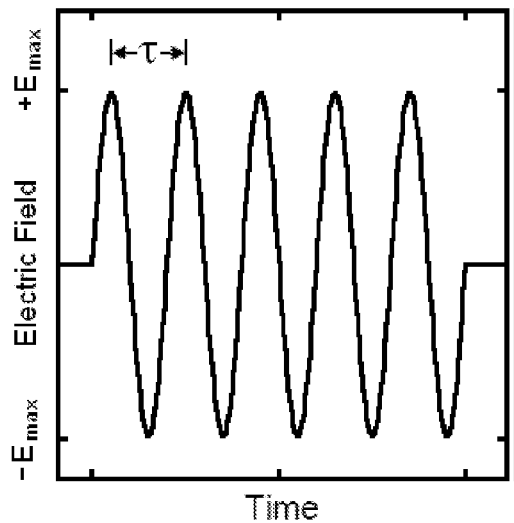
FIG. 2D illustrates an exemplary waveform for modulating impulses that are applied to a nerve according to the present invention.
Figure 2E:
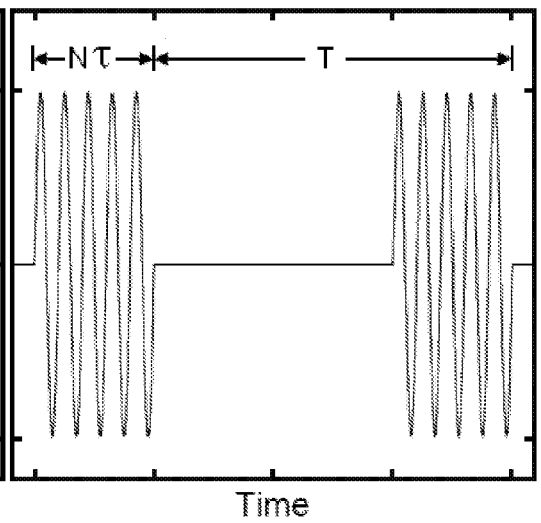
FIG. 2E illustrates another exemplary waveform for modulating impulses that are applied to a nerve according to the present invention.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340 entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2E to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008): 1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2D and 2E may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011]. Those methods involve high-frequency modulation in the range of from about 1.5 KHz to about 50 KHz, which is applied to the patient's spinal cord region. However, such methods are different from the present invention because, for example, they is invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2 (2000):477-509].

Consider now which nerve fibers may be stimulated by the non-invasive vagus nerve stimulation. The waveform disclosed in FIG. 2 contains significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22(Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104 (2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 μm diameter fiber, 12.3 V/m for a 10 μm fiber, and 24.6 V/m for a 5 μm diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110 (2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282 (1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

To summarize the foregoing discussion, the delivery, in a patient suffering from gastroparesis or functional dyspepsia, of an impulse of energy sufficient to stimulate and/or modulate transmission of signals of vagus nerve fibers will result in improved gastric mobility and more normal interoception. The most likely mechanisms do not involve the stimulation of C fibers; and the stimulation of afferent nerve fibers activates neural pathways causing the release of norepinephrine, and/or serotonin and/or GABA.

Figure 8:
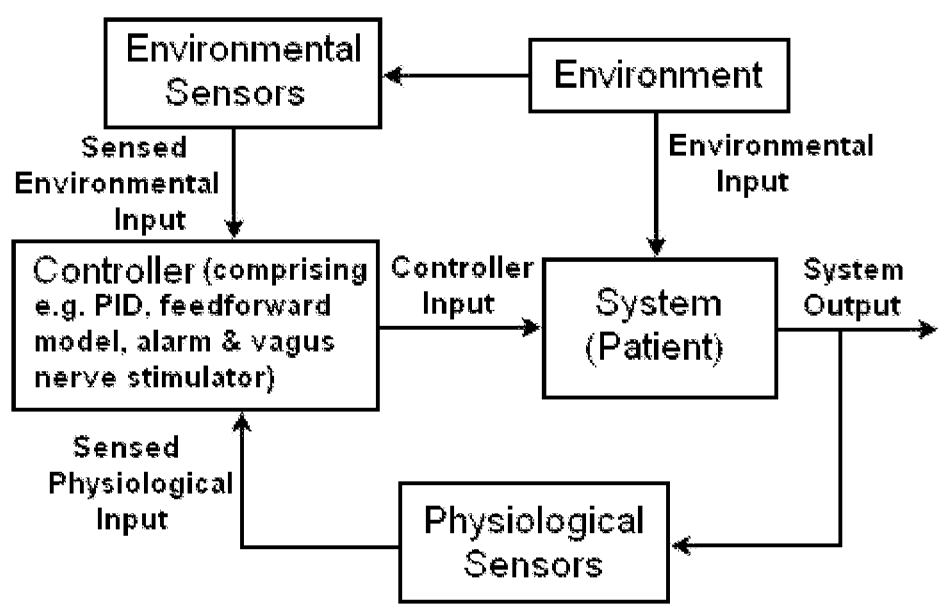
FIG. 8 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 8). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Preferred Embodiments of the Magnetic Stimulator

A preferred embodiment of magnetic stimulator coil 341 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, (UMI Microform Number: 9940153, UMI Company, Ann Arbor Mich.)].

Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e, z and ρ are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions. The shaping of the electric field is described in terms of the corresponding field equations in commonly assigned application US20110125203 (application Ser. No. 12/964,050), entitled Magnetic stimulation devices and methods of therapy, to SIMON et al., which is hereby incorporated by reference.

Thus, the present invention differs from the device disclosed by CARBUNARU and Durand by deliberately shaping an electric field that is used to transcutaneously stimulate the patient. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

In the dissertation cited above, Carbunaru—FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity of the conducting material and select boundary conditions, thereby shaping the electric fields and currents as described above, but also to create devices that can be applied practically to any surface of the body. The volume of the container containing electrically conducting medium is labeled in FIG. 2A as 351. Use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating of the coil(s) and deeper tissue stimulation. However, application of the conducting medium to the surface of the patient is difficult to perform in practice because the tissue contours (head, arms, legs, neck, etc.) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 351 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNA-GEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 341 in FIG. 2A reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain other peripheral nerves.

This preferred embodiment of the magnetic stimulation device is shown in FIG. 3. FIGS. 3A and 3B respectively provide top and bottom views of the outer surface of the toroidal magnetic stimulator 30. FIGS. 3C and 3D respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
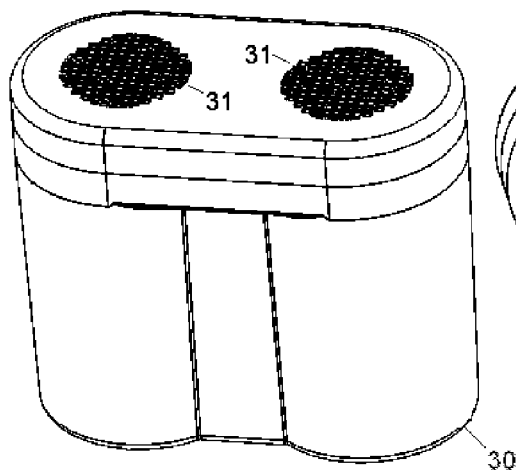
FIG. 3A is a perspective view of the top of a dual-toroid magnetic stimulator coil according to an embodiment of the present invention.
Figure 3B:
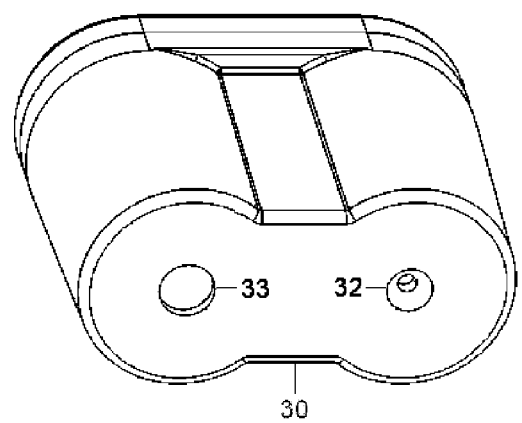
FIG. 3B is a perspective view of the bottom of the dual-toroid magnetic stimulator coil of FIG. 3A.
Figure 3C:
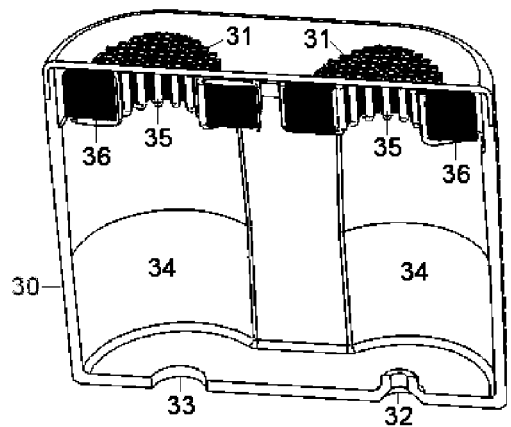
FIG. 3C is a cut-a-way view of the stimulator coil of FIG. 3A.
Figure 3D:
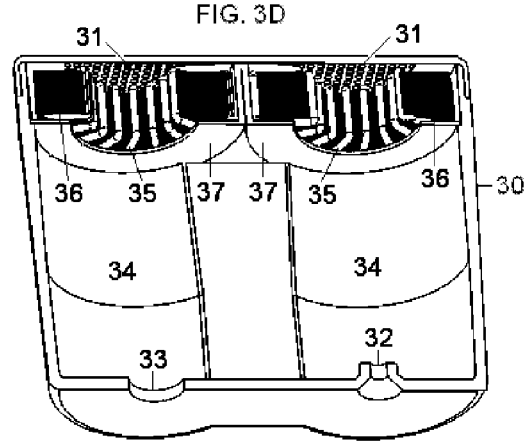
FIG. 3D is a cut-a-way view of the stimulator coil of FIG. 3B.

FIGS. 3B-3D show openings at the opposite end of the stimulator 30. One of the openings is an electronics port 32 through which wires pass from the stimulator coil(s) to the impulse generator (310 in FIG. 2A). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (4, 2001): 434-441].

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Poison]. Conventional magnetic nerve stimulators use a high current impulse generator that may produce discharge currents of 5,000 amps or more, which is passed through the stimulator coil, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology 85 (1992): 253-264; Nafia AL-MUTAWALY, Hubert de Bruin, and Gary Hasey. The effects of pulse configuration on magnetic stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless required to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be required, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.].

Commercially available magnetic stimulators include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 341 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499]. Many of the problems that are associated with such conventional magnetic stimulators, e.g., the complexity of the impulse-generator circuitry and the problem with overheating, are largely avoided by the toroidal design shown in FIG. 3.

Figure 3E:
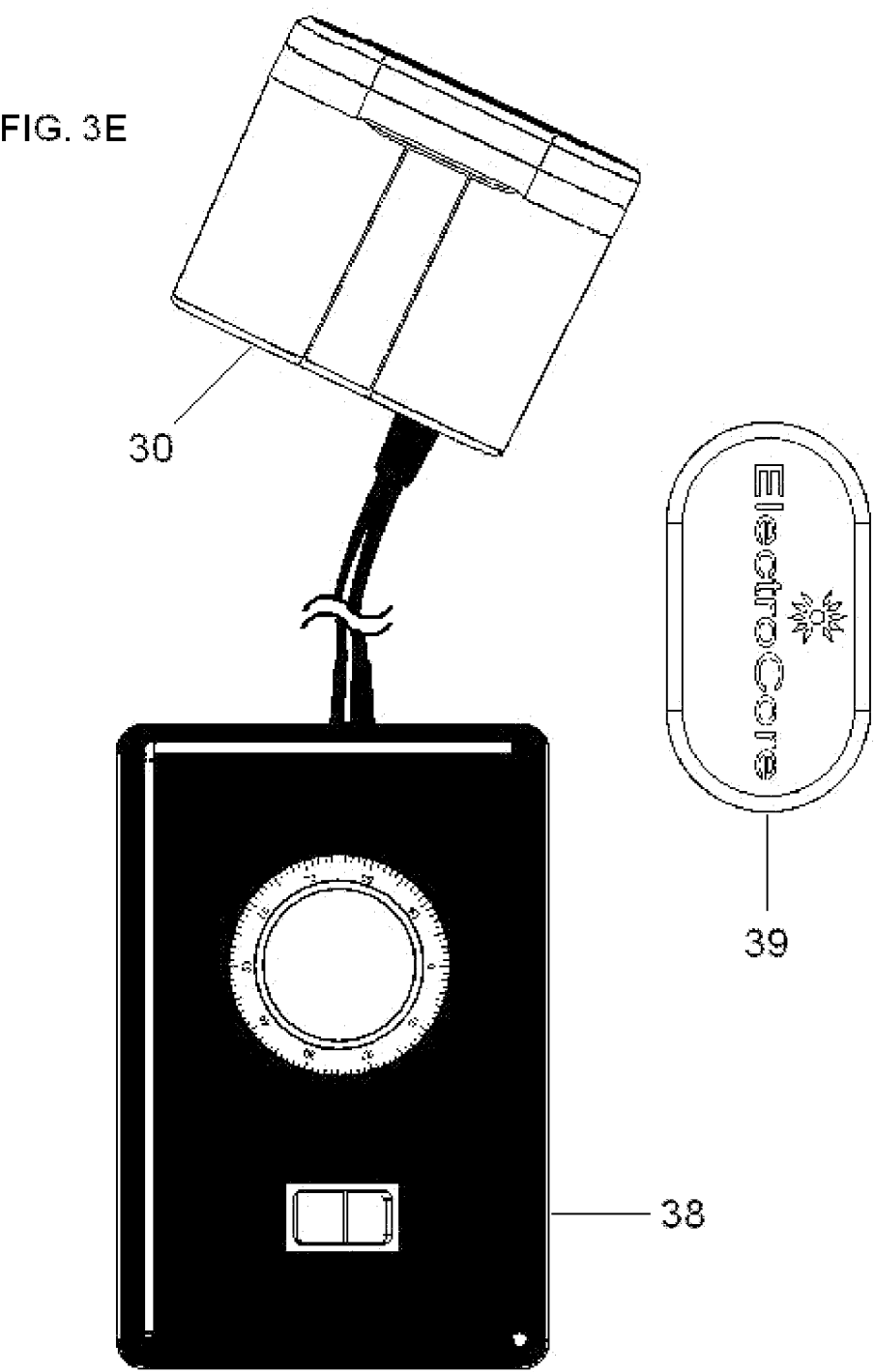
FIG. 3E is an alternative embodiment illustrating the stimulator coil of FIGS. 3A-3D attached to a separate power source.

Thus, use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. Therefore, with the present invention, it is possible to generate waveforms shown in FIG. 2 with relatively simple, low-power circuits that are powered by batteries. The circuits may be enclosed within a box 38 as shown in FIG. 3E, or the circuits may be attached to the stimulator itself (FIG. 3A-3D) to be used as a hand-held device. In either case, control over the unit may be made using only an on/off switch and power knob. The only other component that may be needed might be a cover 39 to keep the conducting fluid from leaking or drying out between uses. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIGS. 2D and 2E, shaping an elongated electrical field of effect.

Preferred Embodiments of the Electrode-Based Stimulator

In another embodiment of the invention, electrodes applied to the surface of the neck, or to some other surface of the body, are used to non-invasively deliver electrical energy to a nerve, instead of delivering the energy to the nerve via a magnetic coil. The vagus nerve has been stimulated previously non-invasively using electrodes applied via leads to the surface of the skin. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of gastroparesis or functional dyspepsia. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of gastroparesis or functional dyspepsia.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. However, none of the disclosures in these patents or patent applications for electrical stimulation of the vagus nerve at the ear are used to treat gastroparesis or functional dyspepsia.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

Considering that the nerve stimulating device 301 in FIG. 2A and the nerve stimulating device 302 in FIG. 2B both control the shape of electrical impulses, their functions are analogous, except that one stimulates nerves via a pulse of a magnetic field, and the other stimulates nerves via an electrical pulse applied through surface electrodes. Accordingly, general features recited for the nerve stimulating device 301 apply as well to the latter stimulating device 302 and will not be repeated here. The preferred parameters for each nerve stimulating device are those that produce the desired therapeutic effects.

Figure 4A:
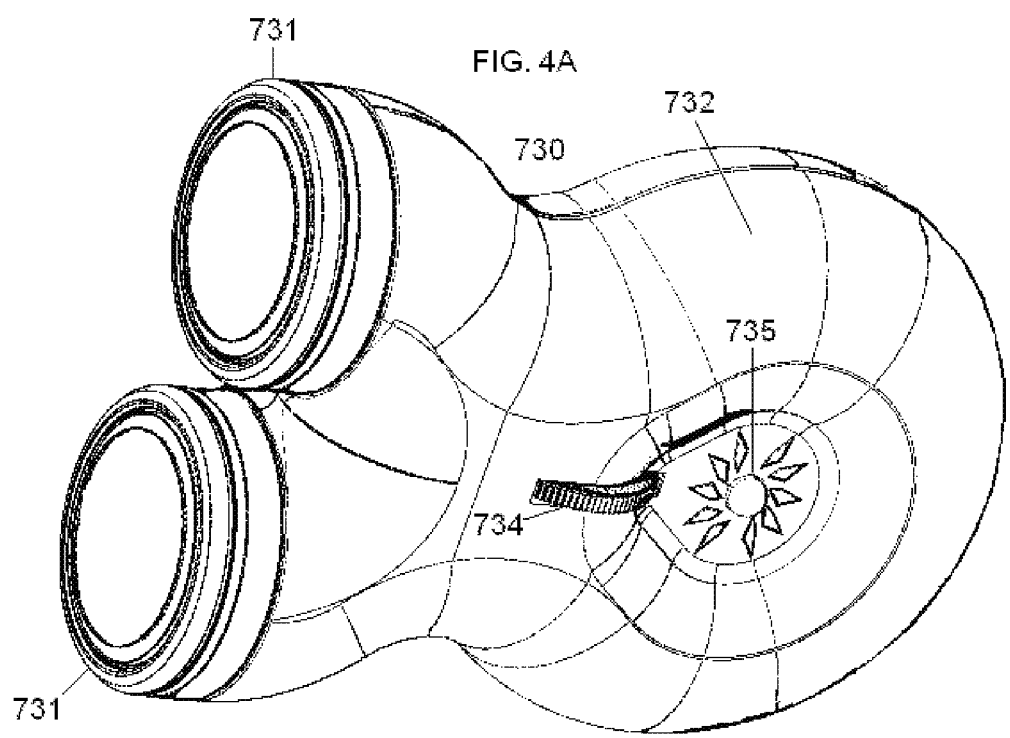
FIG. 4A is a perspective view of a dual-electrode stimulator according to another embodiment of the present invention.
Figure 4B:
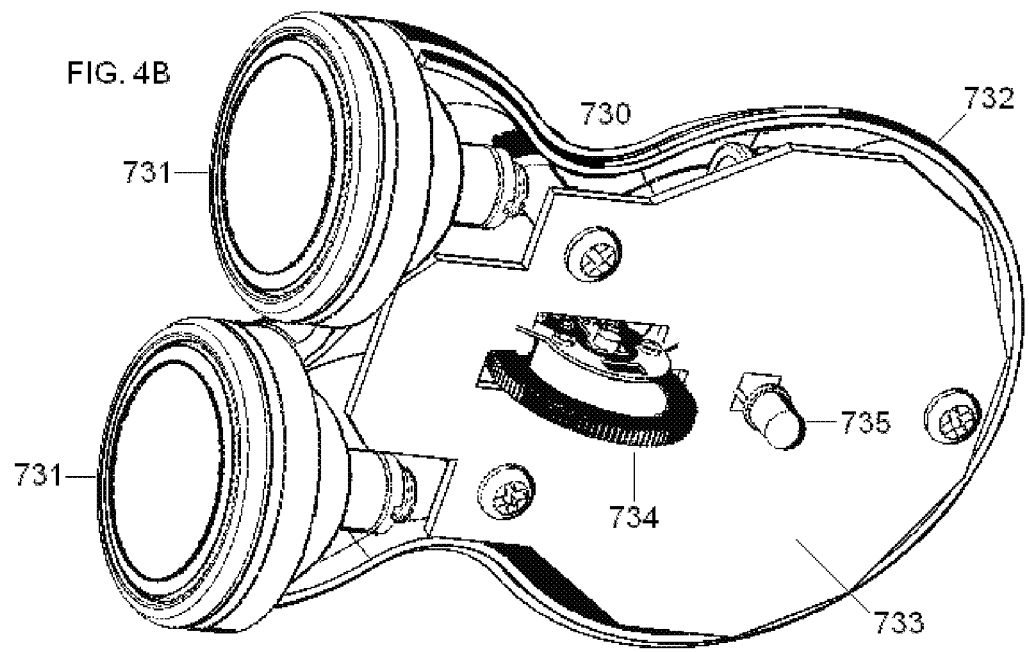
FIG. 4B is a cut-a-way view of the stimulator of FIG. 4A.

A preferred embodiment of an electrode-based stimulator is shown in FIG. 4A. A cross-sectional view of the stimulator along its long axis is shown in FIG. 4B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 4B. However, in other embodiments of the invention, the electronic components that generate the signals that are applied to the electrodes may be separate, but connected to the electrode head (731) using wires. Furthermore, other embodiments of the invention may contain a single such head or more than two heads.

Heads of the stimulator (731) are applied to a surface of the patient's body, during which time the stimulator may be held in place by straps or frames (not shown), or the stimulator may be held against the patient's body by hand. In either case, the level of stimulation power may be adjusted with a wheel (734) that also serves as an on/off switch. A light (735) is illuminated when power is being supplied to the stimulator. An optional cap may be provided to cover each of the stimulator heads (731), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Figure 4C:
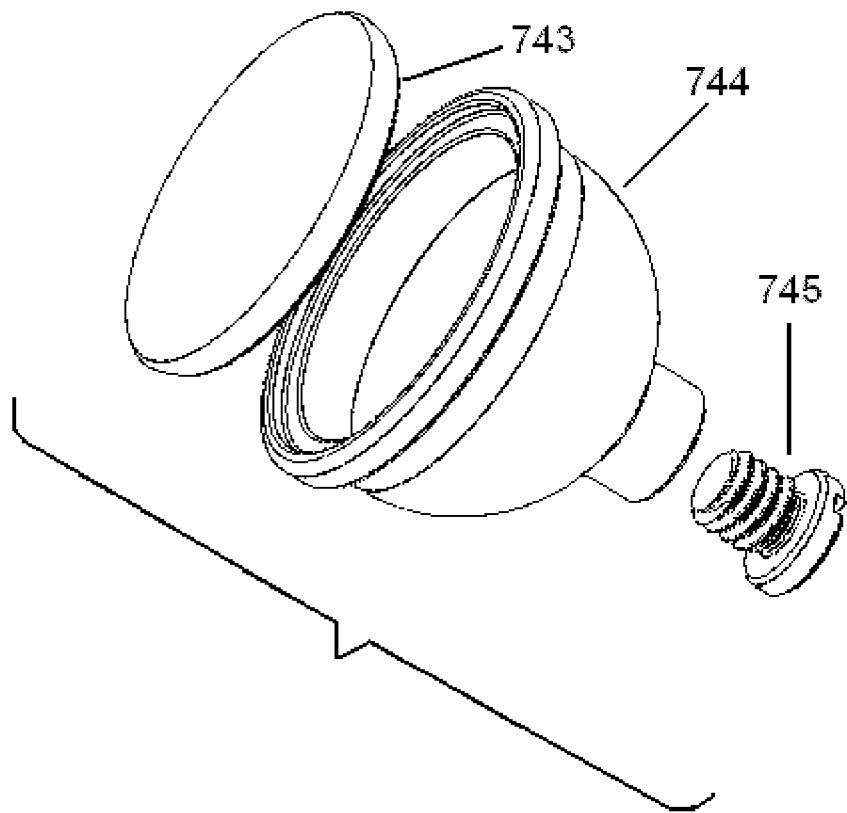
FIG. 4C illustrates a head of the stimulator of FIG. 4A.
Figure 4D:
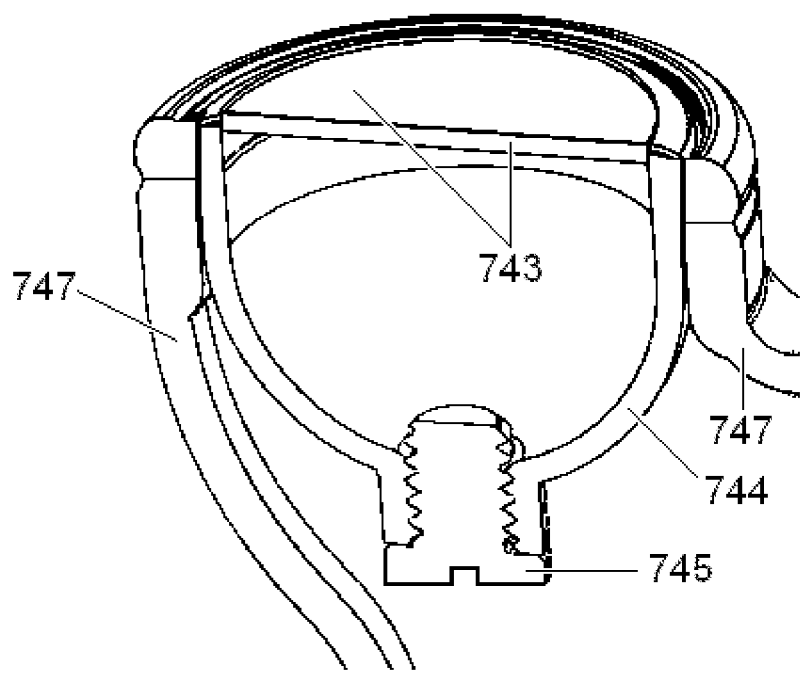
FIG. 4D is a cut-a-way view of the head of FIG. 4C.

Details of one embodiment of the stimulator head are shown in FIGS. 4C and 4D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 2B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 4D, which also shows how the head is attached to the body of the stimulator (747).

If a membrane is used, it ordinarily serves as the interface shown as 351 in FIG. 2B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines Iowa 50321. If the apertures are so-plugged, and the membrane is made of conducting material, the membrane becomes optional, and the plug serves as the interface 351 shown in FIG. 2B.

The head-cup (744) is filled with conducting material (350 in FIG. 2B), for example, SIGNAGEL Electrode Gel from Parker Laboratories, Inc., 286 Eldridge Rd., Fairfield N.J. 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions that determine the electric field strength.

If an outer membrane is used and is made of conducting materials, and the disc (743) in FIG. 4C is made of solid conducting materials such as stainless steel, then the membrane becomes optional, in which case the disc may serve as the interface 351 shown in FIG. 2B. Thus, an embodiment without the membrane is shown in FIGS. 4C and 4D. This version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 2B) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

In certain exemplary embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the surface of the dielectric material (e.g., with isopropyl alcohol or similar disinfectant), avoiding potential contamination during subsequent uses of the device. One such material is a thin sheet of Mylar, supported by a stainless steel disc, as described above.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIG. 2). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113 (1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIG. 2). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25 (1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 2B) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
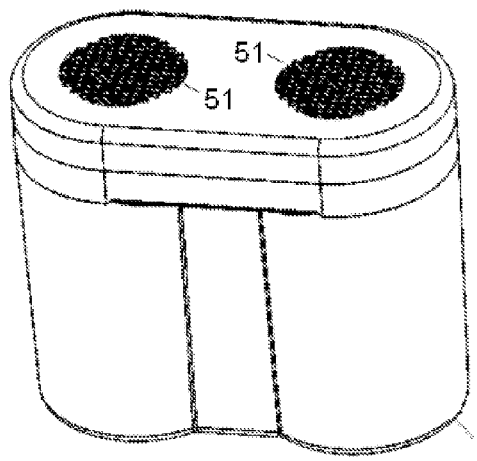
FIG. 5A is a perspective view of the top of a dual-electrode stimulator according to yet another embodiment of the present invention.
Figure 5B:
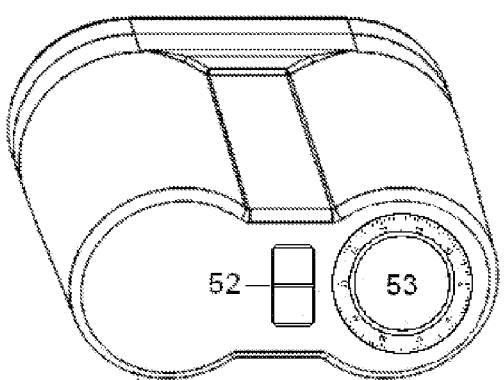
FIG. 5B is a perspective view of the bottom of the stimulator of FIG. 5B.
Figure 5C:
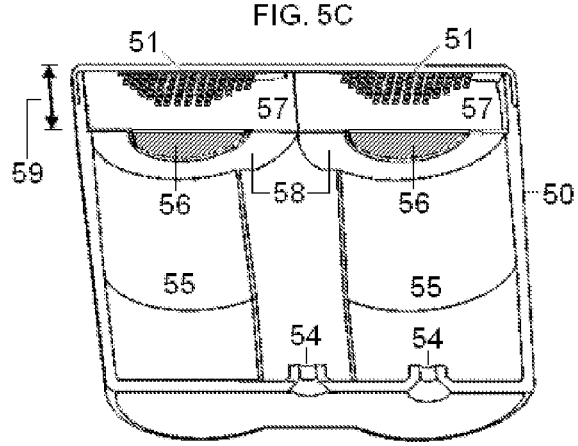
FIG. 5C is a cut-a-way view of the stimulator of FIG. 5A.

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 2B), and the power-level controller is attached to the control unit (330 in FIG. 2B) of the device. The power source battery and power-level controller, as well as the impulse generator (310 in FIG. 2B) are located (but not shown) in the rear compartment 55 of the housing of the stimulator 50.

Individual wires (not shown) connect the impulse generator (310 in FIG. 2B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 2B) to each head compartment 57. An optional nonconducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 2B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, the stimulator's conducting materials may be nonmagnetic, and the stimulator may be connected to the impulse generator by long nonmagnetic wires (345 in FIG. 2B), so that the stimulator may be used in the vicinity of a strong magnetic field, possibly with added magnetic shielding. As another example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 4 and 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-

181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 4 and 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71 (1999): 4944-4950]. In fact, patients found the design shown in FIGS. 4 and 5 to be less painful in a direct comparison with a commercially available grid-pattern electrode [UltraStim grid-pattern electrode, Axelggard Manufacturing Company, 520 Industrial Way, Fallbrook Calif., 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 4 and 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to LeVine; U.S. Pat. No. 6,757, 556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 4 and 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 4 and 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20110230938 (application Ser. No. 13/075,746) entitled Devices and methods for non-invasive electrical stimulation and their use for vagal nerve stimulation on the neck of a patient, to SIMON et al., which is hereby incorporated by reference.

In one embodiment, the magnetic stimulator coil 341 in FIG. 2A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
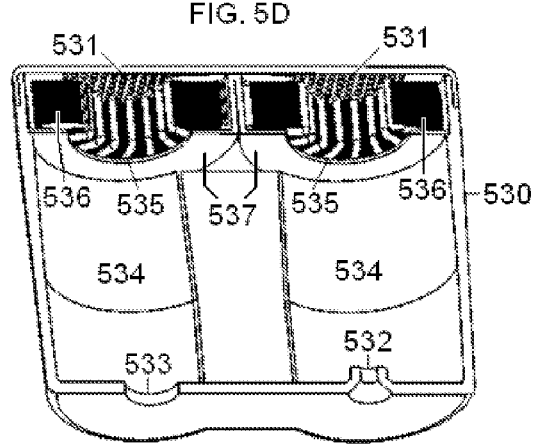
FIG. 5D is a cut-a-way view of the stimulator of FIG. 5B.

As seen in FIG. 5D, a mesh 531 has openings that permit a conducting gel (within 351 in FIG. 2A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 2A). The second opening is a conducting gel port 533 through which conducting gel (351 in FIG. 2A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 2A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
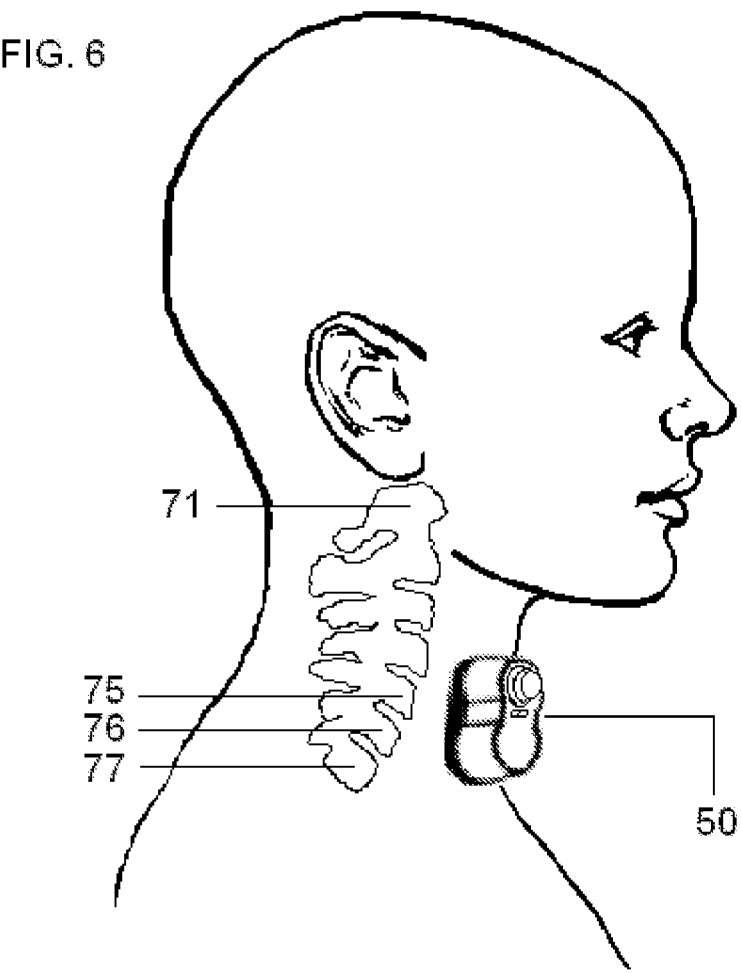
FIG. 6 illustrates the approximate position of the housing of the stimulator according one embodiment of the present invention, when used to stimulate the right vagus nerve in the neck of a patient.

FIG. 6 illustrates use of the devices shown in FIGS. 3, 4 and 5 to stimulate the vagus nerve at that location in the neck, in which the stimulator device 50 or 530 in FIG. 5 is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
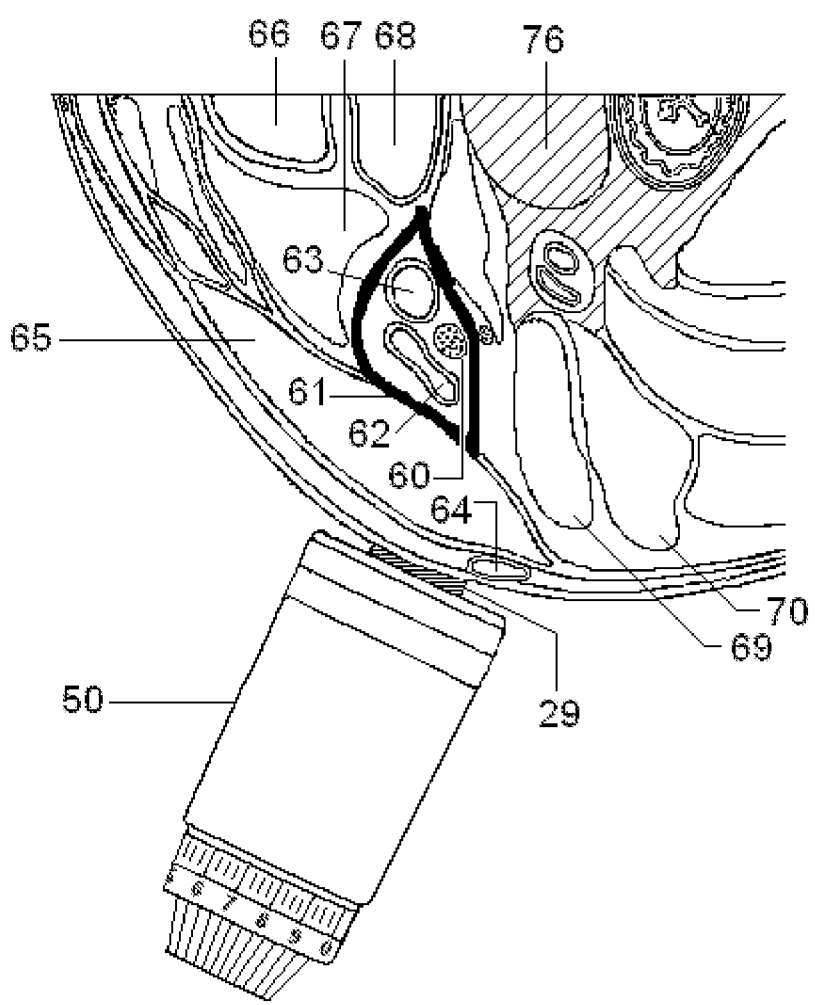
FIG. 7 illustrates the housing of the stimulator according one embodiment of the present invention, when positioned to stimulate a vagus nerve in the patient's neck, wherein the stimulator is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Methods of treating a patient comprise stimulating the vagus nerve as indicated in FIGS. 6 and 7, using the electrical stimulation devices that are disclosed herein. Stimulation may be performed on the left or right vagus nerve or on both of them simultaneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 1 to 1000 microseconds (i.e., about 1 to 10 KHz), preferably 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. For some patients, the stimulation may be performed for 30 minutes, and the treatment is performed several times a week for 12 weeks or longer, because the disease is a chronic situation that requires a substantial period to reverse the pathophysiology. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be selected as the course of the patient's disease changes.

In other embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect.

For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011):101-104; PORTER B A, Khodaparast N, Fayyaz T, Cheung R J, Ahmed S S, Vrana W A, Rennaker R L 2nd, Kilgard M P. Repeatedly pairing vagus nerve stimulation with a movement reorganizes primary motor cortex. Cereb Cortex 22(10, 2012):2365-2374].

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY C R, Sheline Y I, Chibnall J T, George M S, Fletcher J W, Mintun M A. Cerebral blood flow changes during vagus nerve stimulation for depression. Psychiatry Res. 146(2, 2006):179-84]. Thus, by performing the imaging with different sets of stimulation parameters, a database may be constructed, such that the inverse problem of selecting parameters to match a particular brain region may be solved by consulting the database.

Stimulation waveforms may also be constructed by superimposing or mixing the burst waveform shown in FIG. 2, in which each component of the mixture may have a different period T, effectively mixing different burst-per-second waveforms. The relative amplitude of each component of the mixture may be chosen to have a weight according to correlations in different bands in an EEG for a particular resting state network. Thus, MANTINI et al performed simultaneous fMRI and EEG measurements and found that each resting state network has a particular EEG signature [see FIG. 3 in: MANTINI D, Perrucci M G, Del Gratta C, Romani G L, Corbetta M. Electrophysiological signatures of resting state networks in the human brain. Proc Natl Acad Sci USA 104 (32, 2007):13170-13175]. They reported relative correlations in each of the following bands, for each resting state network that was measured: delta (1-4 Hz), theta (4-8 Hz), alpha (8-13 Hz), beta (13-30 Hz), and gamma (30-50 Hz) rhythms. For recently-identified resting state networks, measurement of the corresponding signature EEG networks will have to be performed.

According to the present embodiment of the invention, multiple signals shown in FIG. 2 are constructed, with periods T that correspond to a location near the midpoint of each of the EEG bands (e.g., using the MINATI data, T equals approximately 0.4 sec, 0.1667 sec, 0.095 sec, 0.0465 sec, and 0.025 sec, respectively). A more comprehensive mixture could also be made by mixing more than one signal for each band. These signals are then mixed, with relative amplitudes corresponding to the weights measured for any particular resting state network, and the mixture is used to stimulate the vagus nerve of the patient. Phases between the mixed signals are adjusted to optimize the fMRI signal for the resting state network that is being stimulated. Stimulation of a network may activate or deactivate a network, depending on the detailed configuration of adrenergic receptors within the network and their roles in enhancing or depressing neural activity within the network, as well as subsequent network-to-network interactions. It is understood that variations of this method may be used when different combined fMRI-EEG procedures are employed and where the same resting state may have different EEG signatures, depending on the circumstances [WU C W, Gu H, Lu H, Stein E A, Chen J H, Yang Y. Frequency specificity of functional connectivity in brain networks. Neuroimage 42(3, 2008):1047-1055; LAUFS H. Endogenous brain oscillations and related networks detected by surface EEG-combined fMRI. Hum Brain Mapp 29(7, 2008):762-769; MUSSO F, Brinkmeyer J, Mobascher A, Warbrick T, Winterer G. Spontaneous brain activity and EEG microstates. A novel EEG/fMRI analysis approach to explore resting-state networks. Neuroimage 52(4, 2010):1149-1161; ESPOSITO F, Aragri A, Piccoli T, Tedeschi G, Goebel R, Di Salle F. Distributed analysis of simultaneous EEG-fMRI time-series: modeling and interpretation issues. Magn Reson Imaging 27(8, 2009):1120-1130; FREYER F, Becker R, Anami K, Curio G, Villringer A, Ritter P. Ultrahigh-frequency EEG during fMRI: pushing the limits of imaging-artifact correction. Neuroimage 48(1, 2009):94-108].

The individualized selection of parameters for the nerve stimulation protocol may based on trial and error in order to obtain a beneficial response without the sensation of skin pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve; to avoid potentially dangerous situations such as excessive heart rate; and to maintain measured EEG bands (e.g., delta, theta, alpha, beta) within predetermined ranges, in attempt to preferentially activate particular resting state networks. Thus, with these methods, the parameters of the vagus nerve stimulation may be changed automatically, depending on physiological measurements that are made, in attempt to maintain the values of the physiological signals within predetermined ranges.

The effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMIZATION IN BIOMEDICINE; Nov. 5, 2007, Volume 953, pp. 206-219], but they may exist nevertheless [KOO B. EEG changes with vagus nerve stimulation. J Clin Neurophysiol. 18(5, 2001): 434-41; KUBA R, Guzaninová M, Brázdil M, Novák Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Formaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64].

When stimulating the vagus nerve, motion variability is most often attributable to the patient's breathing, which involves contraction and associated change in geometry of the sternocleidomastoid muscle that is situated close to the vagus nerve (identified as 65 in FIG. 7). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 8 is a control theory representation of the disclosed vagus nerve stimulation methods. As shown there, the patient, or the relevant physiological component of the patient, is considered to be the "System" that is to be controlled. The "System" (patient) receives input from the "Environment." For example, the environment would include ambient temperature, light, and sound. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may include the control unit 330 in FIG. 2. Feedback in the schema shown in FIG. 8 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For monitoring myoelectric activity of the patient's stomach, the sensors may comprise those used for cutaneous electrogastrograms [Zhiyue LIN. Noninvasive diagnosis of delayed gastric emptying from cutaneous electrogastrograms using neural networks. Proceedings of the International Conference on Neural Networks (1, 1997):67-70 (Houston Tex., 9 Jun. 1997-12 Jun. 1997); CHEN J D, Zou X, Lin X, Ouyang S, Liang J. Detection of gastric slow wave propagation from the cutaneous electrogastrogram. Am J Physiol 277(2 Pt 1, 1999):G424-G430; LAWLOR P M, McCullough J A, Byrne P J, Reynolds J V. Electrogastrography: a non-invasive measurement of gastric function. Ir J Med Sci 170(2, 2001):126-131].

Noninvasive methods also exist for the measurement of gastric emptying, some of which would have to be adapted for use in ambulatory monitoring [G R McCLELLAND and J A Sutton. Epigastric impedance: a non-invasive method for the assessment of gastric emptying and motility. Gut 26(6, 1985): 607-614; Masaka SANAKI and Koji Nakada. Stable isotope breath tests for assessing gastric emptying: a comprehensive review. J Smooth Muscle Res 46 (2010):267-280; GREMLICH H U, Martínez V, Kneuer R, Kinzy W, Weber E, Pfannkuche H J, Rudin M. Noninvasive assessment of gastric emptying by near-infrared fluorescence reflectance imaging in mice: pharmacological validation with tegaserod, cisapride, and clonidine. Mol Imaging 3(4, 2004):303-311].

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010):195-212]. In the present application, the features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration.

It may be therapeutically advantageous to program the control unit 330 to control the impulse generator 310 in such a way as to temporally modulate stimulation by the magnetic stimulator coils or electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the gastrointestinal problem that is addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Patent application publication US2009/0177252, entitled Synchronization of vagus nerve stimulation with the cardiac cycle of a patient, to Arthur D. Craig, discloses a method of treating a medical condition in which the vagus nerve is stimulated during a portion of the cardiac cycle and the respiratory cycle. That disclosure pertains to the treatment of a generic medical condition, so it is not specifically directed to the treatment of gastrointestinal problems.

In some embodiments of the invention, overheating of the magnetic stimulator coil may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle.

Furthermore, as an option in the present invention, parameters of the stimulation may be modulated by the control unit 330 to control the impulse generator 310 in such a way as to temporally modulate stimulation by the magnetic stimulator coil or electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil or electrodes, in such a way as to achieve and maintain the blood pressure within predetermined safe or desired limits, by the same method that was indicated above for the heart rate. Thus, even if one does not intend to treat gastrointestinal problems, embodiments of the invention described above may be used to achieve and maintain the heart rate and blood pressure within desired ranges.

Let the measured output variables of the system in FIG. 8 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i = r_i - y_i$ is small, even if there is environmental input or noise to the system. Consider the error function $e_i = r_i - y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

The functional form of the system's input u(t) is constrained to be as shown in FIGS. 2D and 2E. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1, 1998):82-5]. The ultrasound probe is configured to have the same shape as the stimulator, including the attachment of one or more accelerometer. As part of the preliminary protocol, the patient with accelerometers attached is then instructed to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $d\ y_i/dt = F_i(t, \{y_i\}, \{u_j\}, \{v_k\}; \{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form: $u(t) = K_p e(t) + K_i \int_0^t e(\tau)d\tau + K_d de/dt$ where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [L I, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM).3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. To use such a controller, for example, in an attempt to maintain the EEG gamma band at a particular level relative to the alpha band, one could set the integral and derivative gains to zero, increase the proportional gain (amplitude of the stimulation) until the relative gamma band level starts to oscillate, and then measure the period of oscillation. The PID would then be set to its tuned parameter values.

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 8 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

The controller shown in FIG. 8 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 8 may be a type of predictive controller, methods for which have been developed in other contexts as well, such as when a model of the system is used to calculate future outputs of the system, with the objective of choosing among possible inputs so as to optimize a criterion that is based on future values of the system's output variables.

Performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 8 is such the environmental input to the system will have a deleterious effect on the system after a delay, the controller may use this information to provide anticipatory control input to the system, so as to avert or mitigate the deleterious effects that would have been sensed only after-the-fact with a feedback-only controller.

Many patients with gastroparesis and/or functional dyspepsia exhibit symptoms intermittently, but recurrently, in which the patient is asymptomatic for an extended period of time, but then symptoms reappear upon ingestion of a meal. It would be useful to predict when the symptoms will be imminent, so that the patient may perform vagus nerve stimulation as a prophylactic and adjust meal content and portions. A mathematical model of the system is needed in order to perform the predictions of system behavior, e.g., make predictions concerning the onset of symptoms of gastroparesis (and/or functional dyspepsia). Models that are completely based upon physical first principles (white-box) are rare, especially in the case of physiological systems. Instead, most models that make use of prior structural and mechanistic understanding of the system are so-called grey-box models. If the mechanisms of the systems are not sufficiently understood in order to construct a white or grey box model, a black-box model may be used instead. Such black box models comprise autoregressive models [Tim BOLLERSLEV. Generalized autoregressive condiditional heteroskedasticity. Journal of Econometrics 31 (1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48 (1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14 (1998): 35-62].

For the present invention, if a black-box model must be used, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs [Christopher J. C. BURGES. A tutorial on support vector machines for pattern recognition. Data Mining and Knowledge Discovery 2 (1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4(2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

In this example, a training set of physiological data will have been acquired that includes whether or not the patient is experiencing symptoms of gastroparesis (and/or functional dyspepsia). Thus, the classification of the patient's state is whether or not the symptoms are present, and the data used to make the classification consist of the acquired physiological data: electrogastrogram, EEG and its derived features; respiration (abdominal and thoracic plethysmography), carbon dioxide (capnometry with nasual cannula), heart rate (electrocardiogram leads), skin impedance (electrodermal leads), vocalization (microphones), light (light sensor), motion (accelerometer), external and finger temperature (thermometers), etc., as well as parameters of the stimulator device (if it is currently being used on a patient experiencing symptoms), evaluated at $\Delta$ time units prior to the time at which binary "symptoms present" (yes/no) data are acquired, as indicated by the patient or a caregiver. Thus, for a patient who is experiencing symptoms, the SVM is trained to forecast the termination of symptoms, $\Delta$ time units into the future, and the training set includes the time-course of features extracted from the above-mentioned physiological signals. For a patient who is not experiencing symptoms, the SVM is trained to forecast the imminence of symptoms, $\Delta$ time units into the future, and the training set includes the above-mentioned physiological signals. After training the SVM, it is implemented as part of the controller. For patients who are not experiencing symptoms, the controller may sound an alarm and advise the use of vagal nerve stimulation (or other intervention), whenever there is a forecast of imminent symptoms.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating or preventing at least one of gastroparesis or functional dyspepsia in a patient, the method comprising:
   positioning a device adjacent to a skin surface of the patient, wherein the device comprises a housing which houses one or more electrodes, an electrically conductive fluid, and an electrical impulse generator;
   contacting an electrically conductive, non-porous interface coupled to the housing with the skin surface;
   generating, via the electrical impulse generator, one or more shaped electrical impulses at the one or more electrodes within said device; and
   transmitting the one or more shaped electrical impulses from the one or more electrodes through the electrically conductive fluid within the device and then through the electrically conductive, non-porous interface to selected nerve fibers in the patient, wherein the one or more shaped electrical impulses is sufficient to modify at least one of gastroparesis or functional dyspepsia within the patient.

2. The method of claim 1, wherein the one or more shaped electrical impulses is transmitted transcutaneously through an outer skin surface of the patient to generate an electrical impulse at or near the selected nerve fibers.

3. The method of claim 2 further comprising generating an electrical field at or near the device and shaping the electrical field such that the electrical field is sufficient to modulate a nerve fiber at the target region; and wherein the electric field is not sufficient to substantially modulate a nerve or muscle between the outer skin surface and the target region.

4. The method of claim 3 wherein the electric field at the nerve fiber at the target region is from about 10 to about 600 V/m.

5. The method of claim 4 wherein the electric field is less than 100 V/m.

6. The method of claim 3 wherein the nerve fiber at the target region is at least approximately 0.5-2 cm below an outer skin-surface of the patient.

7. The method of claim 1 wherein the selected nerve fibers are associated with a vagus nerve of the patient.

8. The method of claim 1, wherein the one or more shaped electrical impulses comprises bursts of pulses with a frequency from about 1 to about 100 bursts per second.

9. The method of claim 8 wherein each burst contains from 1 to 20 pulses.

10. The method of claim 8 wherein the pulses are full sinusoidal waves.

11. The method of claim 8 wherein each pulse is about 100 to about 1000 microseconds in duration.

12. The method of claim 11 wherein the duration of a pulse within a burst is about 200 microseconds, wherein the number of pulses per burst is from 4 to 6, and wherein the number of bursts per second is from 20 to 30.

13. The method of claim 1 wherein the selected nerve fibers are afferent nerve fibers.

14. The method of claim 1, wherein the one or more shaped electrical impulses generates an electric field at the vagus nerve above a threshold for generating action potentials within A and B fibers of the vagus nerve and below a threshold for generating action potentials within C fibers of the vagus nerve.

15. A method of at least one of treating or preventing at least one of ileus, gastroparesis or functional dyspepsia in a patient, the method comprising:
   positioning a device adjacent to a skin surface of the patient, wherein the device comprises a housing which houses one or more electrodes, an electrically conductive fluid, and an electrical impulse generator;
   contacting an electrically conductive, non-porous interface coupled to the housing with the skin surface;
   generating, via the electrical impulse generator, one or more shaped electrical impulses at the one or more electrodes within said device; and
   transmitting the one or more shaped electrical impulses from the one or more electrodes through the electrically conductive fluid within the device and then through the electrically conductive, non-porous interface to selected nerve fibers in the patient, wherein the one or more shaped electrical impulses is sufficient to modify at least one of ileus, gastroparesis or functional dyspepsia within the patient.

16. A method of at least one of treating or preventing ileus in a patient, the method comprising:
   positioning a device adjacent to a skin surface of the patient, wherein the device comprises a housing which houses one or more electrodes, an electrically conductive fluid, and an electrical impulse generator;
   contacting an electrically conductive, non-porous interface coupled to the housing with the skin surface;
   generating, via the electrical impulse generator, one or more shaped electrical impulses at the one or more electrodes within said device; and
   transmitting the one or more shaped electrical impulses from the one or more electrodes through the electrically conductive fluid within the device and then through the electrically conductive, non-porous interface to selected nerve fibers in the patient, wherein the one or more shaped electrical impulses is sufficient to modify ileus within the patient.

* * * * *